United States Patent
Stancato

(10) Patent No.: US 11,123,326 B2
(45) Date of Patent: Sep. 21, 2021

(54) CHK1/2 INHIBITORS AND IRINOTECAN FOR USE IN THE TREATMENT OF RHABDOMYOSARCOMA

(71) Applicant: Eli Lilly and Company, Indianapolis, IN (US)

(72) Inventor: Louis Frank Stancato, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 216 days.

(21) Appl. No.: 15/742,889

(22) PCT Filed: Jul. 15, 2016

(86) PCT No.: PCT/US2016/042529
§ 371 (c)(1),
(2) Date: Jan. 9, 2018

(87) PCT Pub. No.: WO2017/015124
PCT Pub. Date: Jan. 26, 2017

(65) Prior Publication Data
US 2018/0369202 A1    Dec. 27, 2018

Related U.S. Application Data

(60) Provisional application No. 62/264,059, filed on Dec. 7, 2015, provisional application No. 62/248,408, filed on Oct. 30, 2015, provisional application No. 62/196,087, filed on Jul. 23, 2015.

(51) Int. Cl.
*A61K 31/4155* (2006.01)
*C07D 403/12* (2006.01)
*A61P 35/00* (2006.01)

(52) U.S. Cl.
CPC .......... *A61K 31/4155* (2013.01); *A61P 35/00* (2018.01); *C07D 403/12* (2013.01)

(58) Field of Classification Search
None
See application file for complete search history.

(56) References Cited

U.S. PATENT DOCUMENTS

| | | | |
|---|---|---|---|
| 7,884,126 B2 | 2/2011 | Klein et al. | |
| 8,314,108 B2* | 11/2012 | Farouz | A61K 31/4965 514/255.06 |
| 2005/0158643 A1 | 7/2005 | Yamaguchi et al. | |
| 2011/0144126 A1* | 6/2011 | Farouz | A61K 31/4965 514/255.05 |
| 2013/0231301 A1* | 9/2013 | Davies | A61K 31/437 514/49 |

FOREIGN PATENT DOCUMENTS

WO    2006012308    2/2006

OTHER PUBLICATIONS

Raza et al. (Pharm Pharm Sci, (2014) 1(2), 10, p. 1-10). (Year: 2014).*
Kristina A. Cole, et al, RNAi screen of the protein kinome identifies checkpoint kinase 1 (CHK1) as a therapeutic target in neuroblastoma, PNAS, Feb. 22, 2011, vol. 8, No. 8, pp. 3336-3341.

* cited by examiner

*Primary Examiner* — Taina D Matos Negron
(74) *Attorney, Agent, or Firm* — Quarles & Brady LLP

(57) ABSTRACT

The present invention provides 5-(5-(2-(3-aminopropoxy)-6-methoxyphenyl)-1H-pyrazol-3-ylamino) pyrazine~2~carbonitrile and pharmaceutically acceptable salts and solvates thereof that is capable of inhibiting CHK1 and is useful in the treatment of neuroblastomas and/or soft tissue sarcomas.

8 Claims, No Drawings

CHK1/2 INHIBITORS AND IRINOTECAN FOR USE IN THE TREATMENT OF RHABDOMYOSARCOMA

It is estimated that 20% to 25% of individuals diagnosed with a soft tissue sarcoma have a poor overall survival and a short median survival of 12 months. With regard to neuroblastomas, the outcome for patients with high-risk neuroblastoma remains low, with a long-term survival of less than 50%. Thus, a need exists for novel approaches to treat neuroblastomas and/or soft tissue sarcomas.

CHK1 is a multi-functional protein serine/threonine kinase important for facilitating the DNA damage response and replication fork licensing during DNA synthesis. CHK1 small molecule inhibitors are undergoing clinical investigation for solid tumor and heme malignancies. Because of CHK1's and CHK2's role in DNA damage repair, inhibitors of CHK½ have received interest for use in treating cancer. U.S. Pat. No. 8,314,108, for example, discloses the CHK½ inhibitors 5-(5-(2-(3-aminopropoxy)-6-methoxyphenyl)-1H-pyrazol-3-ylamino)pyrazine-2-carbonitrile, 5-(5-(2-(3-aminopropoxy)-6-methoxyphenyl)-1H-pyrazol-3-ylamino)pyrazine-2-carbonitrile formic acid salt, 5-(5-(2-(3-aminopropoxy)-6-methoxyphenyl)-1H-pyrazol-3-ylamino)pyrazine-2-carbonitrile dihydrogen chloride salt, 5-(5-(2-(3-aminopropoxy)-6-methoxyphenyl)-1H-pyrazol-3-ylamino)pyrazine-2-carbonitrile methanesulfonic acid salt, and 5-(5-(2-(3-aminopropoxy)-6-methoxyphenyl)-1H-pyrazol-3-ylamino)pyrazine-2-carbonitrile methanesulfonic acid monohydrate.

However, there is still a need for CHK1 inhibitors that are potent inhibitors of the cell cycle checkpoints that can act effectively as potentiators of DNA damaging agents which can be beneficial for the treatment of neuroblastomas and/or soft tissue sarcomas. The present invention relates to an aminopyrazole compound, or a pharmaceutically acceptable salt thereof or solvate of the pharmaceutically acceptable salt, that is a potent inhibitor of CHK1 which can be beneficial for the treatment of neuroblastomas and/or soft tissue sarcomas. The compound, or a pharmaceutically acceptable salt thereof or a solvate of the salt, potently abrogates a CHK1 mediated cell cycle arrest induced by treatment with DNA damaging agents in tissue culture and in vivo, which can be beneficial for the treatment of neuroblastomas and/or soft tissue sarcomas. Furthermore, the compound, or a pharmaceutically acceptable salt thereof or a solvate of the salt, of the present invention also provides inhibition of CHK2, which can be beneficial for the treatment of neuroblastomas and/or soft tissue sarcomas. Additionally, the lack of inhibition of certain other protein kinases, such as CDK1, may provide a therapeutic benefit by minimizing undesired effects when using the compound, or a pharmaceutically acceptable salt thereof or solvate of the pharmaceutically acceptable salt, for the treatment of neuroblastomas and/or soft tissue sarcomas.

The present invention also provides an aminopyrazole compound, or a pharmaceutically acceptable salt thereof or a solvate of the pharmaceutically acceptable salt, that is an antagonist of CHK1 and can address the need for more safe and effective treatments of neuroblastomas and/or pediatric and adult soft tissue sarcomas.

The present invention contemplates a use or a method involving 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt for treating neuroblastomas and/or soft tissue sarcomas. Other non-limiting embodiments include 5-(5-(2-(3-aminopropoxy)-6-methoxyphenyl)-1H-pyrazol-3-ylamino)pyrazine-2-carbonitrile formic acid salt, 5-(5-(2-(3-aminopropoxy)-6-methoxyphenyl)-1H-pyrazol-3-ylamino)pyrazine-2-carbonitrile dihydrogen chloride salt, 5-(5-(2-(3-aminopropoxy)-6-methoxyphenyl)-1H-pyrazol-3-ylamino)pyrazine-2-carbonitrile methanesulfonic acid salt, and 5-(5-(2-(3-aminopropoxy)-6-methoxyphenyl)-1H-pyrazol-3-ylamino)pyrazine-2-carbonitrile methanesulfonic acid monohydrate for use in treating or as a method of treating neuroblastomas and/or soft tissue sarcomas.

As a particular embodiment, the present invention provides the compound which is 5-(5-(2-(3-aminopropoxy)-6-methoxyphenyl)-1H-pyrazol-3-ylamino)pyrazine-2-carbonitrile for use in treating or as a method of treating neuroblastomas and/or soft tissue sarcomas.

The present invention provides the formic acid, dihydrogen chloride, and methanesulfonic acid salts of 5-(5-(2-(3-aminopropoxy)-6-methoxyphenyl)-1H-pyrazol-3-ylamino)pyrazine-2-carbonitrile for use in treating or as a method of treating neuroblastomas and/or soft tissue sarcomas.

The present invention also provides the compound which is 5-(5-(2-(3-aminopropoxy)-6-methoxyphenyl)-1H-pyrazol-3-ylamino)pyrazine-2-carbonitrile methanesulfonic acid monohydrate for use in treating or as a method of treating neuroblastomas and/or soft tissue sarcomas.

The present invention provides 5-(5-(2-(3-aminopropoxy)-6-methoxyphenyl)-1H-pyrazol-3-ylamino)pyrazine-2-carbonitrile methanesulfonic acid monohydrate in crystalline form characterized by a X-ray powder diffraction pattern having peaks at 2θ±0.02°=12.640, 21.25°, and 26.150 for use in treating or as a method of treating neuroblastomas and/or soft tissue sarcomas.

The present invention contemplates a use or a method involving 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt for treating neuroblastomas and/or soft tissue sarcomas, but not liposarcomas. Other non-limiting embodiments include 5-(5-(2-(3-aminopropoxy)-6-methoxyphenyl)-1H-pyrazol-3-ylamino)pyrazine-2-carbonitrile formic acid salt, 5-(5-(2-(3-aminopropoxy)-6-methoxyphenyl)-1H-pyrazol-3-ylamino)pyrazine-2-carbonitrile dihydrogen chloride salt, 5-(5-(2-(3-aminopropoxy)-6-methoxyphenyl)-1H-pyrazol-3-ylamino)pyrazine-2-carbonitrile methanesulfonic acid salt, and 5-(5-(2-(3-aminopropoxy)-6-methoxyphenyl)-1H-pyrazol-3-ylamino)pyrazine-2-carbonitrile methanesulfonic acid monohydrate for use in treating or as a method of treating neuroblastomas and/or soft tissue sarcomas, but not liposarcomas.

As a particular embodiment, the present invention provides the compound which is 5-(5-(2-(3-aminopropoxy)-6-methoxyphenyl)-1H-pyrazol-3-ylamino)pyrazine-2-carbonitrile for use in treating or as a method of treating neuroblastomas and/or soft tissue sarcomas, but not liposarcomas.

The present invention provides the formic acid, dihydrogen chloride, and methanesulfonic acid salts of 5-(5-(2-(3-aminopropoxy)-6-methoxyphenyl)-1H-pyrazol-3-ylamino)pyrazine-2-carbonitrile for use in treating or as a method of treating neuroblastomas and/or soft tissue sarcomas, but not liposarcomas.

The present invention also provides the compound which is 5-(5-(2-(3-aminopropoxy)-6-methoxyphenyl)-1H-pyrazol-3-ylamino)pyrazine-2-carbonitrile methanesulfonic acid monohydrate for use in treating or as a method of treating neuroblastomas and/or soft tissue sarcomas, but not liposarcomas.

The present invention provides 5-(5-(2-(3-aminopropoxy)-6-methoxyphenyl)-1H-pyrazol-3-ylamino)pyrazine-2-carbonitrile methanesulfonic acid monohydrate in crystalline form characterized by a X-ray powder diffraction pattern having peaks at 2θ±0.02°=12.640, 21.25°, and 26.15° for use in treating or as a method of treating cancers including neuroblastomas and/or soft tissue sarcomas, but not liposarcomas.

The present invention provides a pharmaceutical composition comprising 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, and one or more of a pharmaceutically acceptable carrier, diluent, or excipient for use in treating or as a method of treating neuroblastomas and/or soft tissue sarcomas. The present invention provides a pharmaceutical composition comprising 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, and one or more of a pharmaceutically acceptable carrier, diluent, or excipient for use in treating or as a method of treating neuroblastomas and/or soft tissue sarcomas, but not liposarcomas. The present invention provides a pharmaceutical composition comprising 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, and one or more of a pharmaceutically acceptable carrier, diluent, or excipient for use in treating or as a method of treating cancer; wherein the cancer is selected from the group consisting of neuroblastoma, rhabdomyosarcoma, osteosarcoma, Ewing's sarcoma, desmoplastic small round cell tumor, and leiomyosarcoma.

The present invention provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt; wherein the cancer is selected from the group consisting of neuroblastoma, rhabdomyosarcoma, osteosarcoma, Ewing's sarcoma, desmoplastic small round cell tumor, and leiomyosarcoma. In addition, the present invention also provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, and ionizing radiation; wherein the cancer is selected from the group consisting of neuroblastoma, rhabdomyosarcoma, osteosarcoma, Ewing's sarcoma, desmoplastic small round cell tumor, and leiomyosarcoma. The present invention provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, and at least one chemotherapy agent; wherein the cancer is selected from the group consisting of neuroblastoma, rhabdomyosarcoma, osteosarcoma, Ewing's sarcoma, desmoplastic small round cell tumor, and leiomyosarcoma. The present invention provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, at least one chemotherapy agent, and ionizing radiation; wherein the cancer is selected from the group consisting of neuroblastoma, rhabdomyosarcoma, osteosarcoma, Ewing's sarcoma, desmoplastic small round cell tumor, and leiomyosarcoma.

The present invention provides the use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for the manufacture of a medicament for the treatment of cancer; wherein the cancer is selected from the group consisting of neuroblastoma, rhabdomyosarcoma, osteosarcoma, Ewing's sarcoma, desmoplastic small round cell tumor, and leiomyosarcoma. In addition, the present invention also provides the use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for the manufacture of a medicament for the treatment of cancer wherein said treatment comprises combination therapy with ionizing radiation; wherein the cancer is selected from the group consisting of neuroblastoma, rhabdomyosarcoma, osteosarcoma, Ewing's sarcoma, desmoplastic small round cell tumor, and leiomyosarcoma. The present invention provides the use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for the manufacture of a medicament for the treatment of cancer by combination therapy wherein said combination therapy treatment comprises administration of said medicament and administration of one or more other chemotherapy agents to the same patient; wherein the cancer is selected from the group consisting of neuroblastoma, rhabdomyosarcoma, osteosarcoma, Ewing's sarcoma, desmoplastic small round cell tumor, and leiomyosarcoma. The present invention provides the use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for the manufacture of a medicament for the treatment of cancer by combination therapy wherein said combination therapy treatment comprises administration of said medicament and administration of one or more other chemotherapy agents and ionizing radiation to the same patient; wherein the cancer is selected from the group consisting of neuroblastoma, rhabdomyosarcoma, osteosarcoma, Ewing's sarcoma, desmoplastic small round cell tumor, and leiomyosarcoma.

The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for use in therapy. The present invention also provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for use in the treatment of cancer.

In addition, the present invention also provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, for use in simultaneous, separate, or sequential combination with ionizing radiation in the treatment of cancer. Furthermore, the present invention also provides 5-(5-(2-(3-aminopropoxy)-

6-methoxyphenyl)-1H-pyrazol-3-ylamino)pyrazine-2-carbonitrile, or a pharmaceutically acceptable salt thereof or a solvate of the salt, for use in simultaneous, separate, or sequential combination with one or more chemotherapy agents in the treatment of cancer.

The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for use in the treatment of cancer; wherein the cancer is selected from the group consisting of neuroblastoma, rhabdomyosarcoma, osteosarcoma, Ewing's sarcoma, desmoplastic small round cell tumor, and leiomyosarcoma. In addition, the present invention also provides 5-(5-(2-(3-aminopropoxy)-6-methoxyphenyl)-1H-pyrazol-3-ylamino) pyrazine-2-carbonitrile, or a pharmaceutically acceptable salt thereof or a solvate of the pharmaceutically acceptable salt, for use in simultaneous, separate, or sequential combination with ionizing radiation in the treatment of cancer; wherein the cancer is selected from the group consisting of neuroblastoma, rhabdomyosarcoma, osteosarcoma, Ewing's sarcoma, desmoplastic small round cell tumor, and leiomyosarcoma. The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for use in simultaneous, separate, or sequential combination with one or more chemotherapy agents in the treatment of cancer; wherein the cancer is selected from the group consisting of neuroblastoma, rhabdomyosarcoma, osteosarcoma, Ewing's sarcoma, desmoplastic small round cell tumor, and leiomyosarcoma. The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for use in simultaneous, separate, or sequential combination with one or more chemotherapy agents and ionizing radiation in the treatment of cancer; wherein the cancer is selected from the group consisting of neuroblastoma, rhabdomyosarcoma, osteosarcoma, Ewing's sarcoma, desmoplastic small round cell tumor, and leiomyosarcoma.

The present invention provides use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for the manufacture of a medicament for the treatment of cancer, wherein the medicament is to be administered simultaneously, separately or sequentially with ionizing radiation; wherein the cancer is selected from the group consisting of neuroblastoma, rhabdomyosarcoma, osteosarcoma, Ewing's sarcoma, desmoplastic small round cell tumor, and leiomyosarcoma.

The present invention provides use of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for the manufacture of a medicament for the treatment of cancer, wherein the medicament also comprises at least one chemotherapy agent or is to be administered simultaneously, separately or sequentially with the at least one chemotherapy agent; wherein the cancer is selected from the group consisting of neuroblastoma, rhabdomyosarcoma, osteosarcoma, Ewing's sarcoma, desmoplastic small round cell tumor, and leiomyosarcoma.

The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for use in simultaneous, separate or sequential combination with ionizing radiation in the treatment of cancer; wherein the cancer is selected from the group consisting of neuroblastoma, rhabdomyosarcoma, osteosarcoma, Ewing's sarcoma, desmoplastic small round cell tumor, and leiomyosarcoma.

The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for use in simultaneous, separate or sequential combination with at least one chemotherapy agent in the treatment of cancer; wherein the cancer is selected from the group consisting of neuroblastoma, rhabdomyosarcoma, osteosarcoma, Ewing's sarcoma, desmoplastic small round cell tumor, and leiomyosarcoma.

The present invention provides 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, for use in simultaneous, separate or sequential combination with at least one chemotherapy agent and ionizing radiation in the treatment of cancer; wherein the cancer is selected from the group consisting of neuroblastoma, rhabdomyosarcoma, osteosarcoma, Ewing's sarcoma, desmoplastic small round cell tumor, and leiomyosarcoma.

The present invention provides a pharmaceutical composition comprising 5-(5-(2-(3-aminopropoxy)-6-methoxyphenyl)-1H-pyrazol-3-ylamino)pyrazine-2-carbonitrile, or a pharmaceutically acceptable salt thereof or a solvate of the pharmaceutically acceptable salt, together with a pharmaceutically acceptable carrier and optionally other therapeutic ingredients; wherein the cancer is selected from the group consisting of neuroblastoma, rhabdomyosarcoma, osteosarcoma, Ewing's sarcoma, desmoplastic small round cell tumor, and leiomyosarcoma.

5-(5-(2-(3-aminopropoxy)-6-methoxyphenyl)-1H-pyrazol-3-ylamino)pyrazine-2-carbonitrile methanesulfonic acid monohydrate is a CHK1/CHK2 small molecule inhibitor that as a single agent, generates double-stranded DNA breaks during S-Phase, leading to replication catastrophe and eventually mitotic catastrophe. In addition, 5-(5-(2-(3-aminopropoxy)-6-methoxyphenyl)-1H-pyrazol-3-ylamino) pyrazine-2-carbonitrile methanesulfonic acid monohydrate mediated inhibition of CHK1 abrogates the DNA damage response following treatment with genotoxics such as doxorubicin and gemcitabine, enhancing DNA damage and the apoptotic response to these agents.

The efficacy of 5-(5-(2-(3-aminopropoxy)-6-methoxyphenyl)-1H-pyrazol-3-ylamino)pyrazine-2-carbonitrile methanesulfonic acid monohydrate is measurable in vivo in mouse models of neuroblastomas and human pediatric and adult sarcomas. 5-(5-(2-(3-Aminopropoxy)-6-methoxyphenyl)-1H-pyrazol-3-ylamino)pyrazine-2-carbonitrile methanesulfonic acid monohydrate (10 mg/kg) can be administered subcutaneously to nude mice bearing either cell-derived xenografts (CDX) or patient-derived xenografts (PDX) of human rhabdomyosarcoma, desmoplastic small round cell tumor (DSRCT), osteosarcoma, and Ewing's sarcoma using a 3 day on, 4 day off b.i.d. dosing schedule. Tumor volume and body weight can be measured two times per week. Tumor-specific parameters can be evaluated by immunohistochemistry.

5-(5-(2-(3-Aminopropoxy)-6-methoxyphenyl)-1H-pyrazol-3-ylamino)pyrazine-2-carbonitrile methanesulfonic acid monohydrate elicits strong single agent activity in 7/13 pediatric tumor models, ranging from stable disease to complete regression. Of note, a complete regression is observed in a PDX model of DSRCT following four dosing cycles. Upon cessation of therapy, tumor growth is observed 50 days post-treatment, including tumor regression when re-challenged with 5-(5-(2-(3-aminopropoxy)-6-methoxyphenyl)-1H-pyrazol-3-ylamino)pyrazine-2-carbonitrile methanesulfonic acid monohydrate in the PDX model of DSRCT. In the SJCRH-30 aRMS model, the complete regression that is observed during treatment is immediately reversed upon withdrawal of the drug, and subsequent regrowth is resistant to further treatment with 5-(5-(2-(3-aminopropoxy)-6-methoxyphenyl)-1H-pyrazol-3-ylamino)pyrazine-2-carbonitrile methanesulfonic acid monohydrate at 10 mg/kg. However, in this same model, 5-(5-(2-(3-aminopropoxy)-6-methoxyphenyl)-1H-pyrazol-3-ylamino)pyrazine-2-carbonitrile methanesulfonic acid monohydrate plus doxorubicin leads to a durable, complete regression with no detectable tumor growth for greater than two months after cessation of therapy.

5-(5-(2-(3-Aminopropoxy)-6-methoxyphenyl)-1H-pyrazol-3-ylamino)pyrazine-2-carbonitrile methanesulfonic acid monohydrate was also active in PDX models of leiomyosarcoma, but not liposarcoma. 5-(5-(2-(3-Aminopropoxy)-6-methoxyphenyl)-1H-pyrazol-3-ylamino)pyrazine-2-carbonitrile methanesulfonic acid monohydrate alone and in combination with chemotherapy can significantly impede the growth of human PDX and CDX models of sarcoma.

The present invention relates to an aminopyrazole compound, or a pharmaceutically acceptable salt thereof or a solvate of the pharmaceutically acceptable salt that inhibits CHK1 and is useful for treating cancers characterized by defects in deoxyribonucleic acid (DNA) replication, chromosome segregation, or cell division.

Non-limiting examples of chemotherapy agents include 5-fluorouracil, hydroxyurea, gemcitabine, methotrexate, pemetrexed, doxorubicin, dactinomycin, etoposide, vincristine, ifosfamide, irinotecan, cyclophosphamide, cisplatin, taxol, and combinations thereof. Embodiments of the methods and uses described herein include other cancers selected from the group consisting of bladder cancer, colon cancer, gastric cancer, liver cancer, lung cancer, mammary cancer, melanoma, ovarian cancer, pancreatic cancer, mesothelioma, renal cancer, and uterine cancer. Furthermore, the present invention provides embodiments of the methods and uses as described herein, in which the rhabdomyosarcoma is alveolar rhabdosarcoma and/or embryonal rhabdomyosarcoma.

The compound, or a pharmaceutically acceptable salt thereof or a solvate of the salt, of the present invention may exist as tautomeric forms. When tautomeric forms exist, each form and mixtures thereof, are contemplated in the present invention.

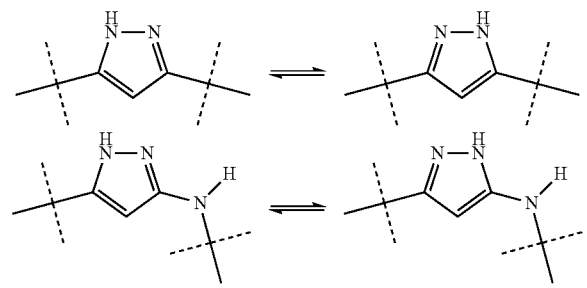

Unless otherwise defined, this invention includes pharmaceutically acceptable salts of the compound of Example 3 as well as solvates of the free base of the compound of Example 3 or a pharmaceutically acceptable salt thereof. The term "pharmaceutically acceptable salt" as used herein, refers to salts of the compound of Example 3. Examples of pharmaceutically acceptable salts and methods for their preparation are conventional in the art. See for example, Stahl et al., "Handbook of Pharmaceutical Salts: Properties, Selection and Use", VCHA/Wiley-VCH, (2002); Gould, P. L., "Salt selection for basic drugs", *International Journal of Pharmaceutics*, 33: 201-217 (1986); and Bastin et al. "Salt Selection and Optimization Procedures for Pharmaceutical New Chemical Entities", *Organic Process Research and Development*, 4: 427-435 (2000).

In addition to pharmaceutically acceptable salts, other salts are included in the invention. They may serve as intermediates in the purification of compounds or in the preparation of other pharmaceutically-acceptable salts, or are useful for identification, characterization, or purification.

As used herein, the term "patient" refers to a human or nonhuman mammal. More particularly, the term "patient" refers to a human.

The term "treating" (or "treat" or "treatment") refers to the process involving a slowing, interrupting, arresting, controlling, reducing, or reversing the progression or severity of a symptom, disorder, condition, or disease.

As used herein, the term "effective amount" refers to the amount or dose of the compound, or a pharmaceutically acceptable salt thereof or a solvate of the salt, of the present invention, described herein, alone or in combination with ionizing radiation or a chemotherapy agent which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the co-administration of other agents, if needed; the specific disease involved; the degree or severity of the disease; the response of the individual patient; the particular compound administered; the mode of administration; the bioavailability characteristics of the preparation administered; the dose regimen selected; the use of any concomitant medications; and other relevant circumstances. While not to be construed as limiting the present invention in any way, 20-150 mg/m$^2$ represents an effective amount of the compound, or a pharmaceutically acceptable salt thereof or a solvate of the salt, described herein.

As used herein, the term "combination therapy" refers to separate, simultaneous, or sequential administration of the compound, or a pharmaceutically acceptable salt thereof or a solvate of the salt, of the present invention and at least one chemotherapy agent. Furthermore, the term "combination therapy" refers to separate, simultaneous, or sequential administration of the compound, or a pharmaceutically acceptable salt thereof or a solvate of the salt, of the present invention and ionizing radiation. The term "combination therapy" also refers to separate, simultaneous, or sequential administration of the compound, or a pharmaceutically acceptable salt thereof or a solvate of the salt, of the present invention, ionizing radiation, and at least one chemotherapy agent.

One of ordinary skill in the art will recognize that 5-(5-(2-(3-aminopropoxy)-6-methoxyphenyl)-1H-pyrazol-3-ylamino)pyrazine-2-carbonitrile methanesulfonic acid monohydrate can alternatively be referred to as 2-pyrazinecarbonitrile, 5-[[5-[2-(3-aminopropoxy)-6-methoxyphenyl]-1H-pyrazol-3-yl]amino]monomesylate monohydrate.

The compound of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, may be formulated for administration as part of a pharmaceutical composition. As such, pharmaceutical compositions comprising the compound of 5-(5-(2-(3-aminopropoxy)-6-methoxyphenyl)-1H-pyrazol-3-ylamino)pyrazine-2-carbonitrile, or a pharmaceutically acceptable salt thereof or a solvate of the salt, in combination with one or more pharmaceutically acceptable carriers, excipients, or diluents are an important embodiment of the invention. Examples of pharmaceutical compositions and methods for their preparation are well known in the art. See, e.g. REMINGTON: THE SCIENCE AND PRACTICE OF PHARMACY, A. Gennaro, et al., eds., 22$^{nd}$ ed., Pharmaceutical Press (2012).

The compound, or a pharmaceutically acceptable salt thereof or a solvate of the salt, of the present invention can be administered by any route which makes it bioavailable. For example, the compound, or a pharmaceutically acceptable salt thereof or a solvate of the salt, can be administered orally, subcutaneously, intramuscularly, intravenously, transdermally, topically, intranasally, rectally, buccally, and the like. Alternatively, the compound, or a pharmaceutically acceptable salt thereof or a solvate of the salt, may be administered by infusion. IV infusion is the preferred route of administration.

As used herein, the following terms have the meanings indicated: "ATCC" refers to American Type Culture collection; "ATM" refers to Ataxia telangiectasia mutated; "ATP" refers to adenosine triphosphate; "ATR" refers to Ataxia- and Rad related kinases; "BCA" refers to bicinchoninic acid; "b.i.d." refers to twice a day dosing; "Boc or t-Boc" refers to tert-butoxycarbonyl; "BSA" refers to bovine serum albumin; "CTG" refers to Cell Titer Glow reagent; "DPBS" refers to Dulbecco's phosphate-buffered saline; "DIAD" refers to diisopropyl azodicarboxylate; "DMF" refers to dimethylformamide; "DMSO" refers to dimethylsulfoxide; "DTT" refers to dithiothreitol; "DSRCT" refers to desmoplastic small round cell tumor; "EDTA" refers to ethylenediamine tetraacetic acid; "ERK" refers to extracellular signal-regulated kinases; "EtOH" refers to ethanol; "EWS" refers to Ewing's sarcoma; "FBS" refers to fetal bovine serum; "G2M" refers to the G2 and M phases of the cell cycle; "HBSS" refers to Hank's Balanced Salt Solution; "HEPES" refers to N-2-hydroxyethylpiperazine-N'-2-ethanesulfonic acid; "hnRNP" refers to heterogeneous nuclear ribonucleoprotein; "HRP" refers to horseradish peroxidase; "LMS" refers to leiomyosarcoma; "MEM" refers to minimum essential medium; "MeOH" refers to methanol or methyl alcohol; "NBM" refers to neuroblastoma; "OS" refers to osteosarcoma; "PBS" refers to phosphate-buffered saline; "PBST" refers to phosphate-buffered saline Tween-20, "Ph" refers to phenyl; "pHH3" refers to phosphorylated histone H3; "PI" refers to propidium iodide; "PKC" refers to protein kinase C; "RMS" refers to rhabdomyosarcoma; "RNAase" refers to ribonuclease A; "RPMI" refers to Roswell Park Memorial Institute; "SDS" refers to sodium dodecyl sulfate; "ST" refers to soft tissue; "TBST" refers to tris-buffered saline Tween-20; "THF" refers to tetrahydrofuran; "TR-FRET" refers to time resolved fluorescent energy transfer; "Tris" refers to tris(hydroxymethyl) aminomethane; "Triton™-X" refers to 4-(1,1,3,3-tetramethylbutyl)phenyl-polyethylene glycol t-octylphenoxypolyethoxyethanol polyethylene glycol tert-octylphenyl ether; and "Tween-20" refers to polysorbate 20.

The following Preparations and Examples are provided to illustrate the invention in further detail and represent typical syntheses of the compound, or a pharmaceutically acceptable salt thereof or a solvate of the salt.

Route A

Preparation 1

5-Isothiocyanatopyrazine-2-carbonitrile

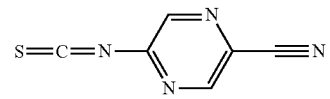

A solution of thiophosgene (1.86 g, 15 mmol) in THF (4 mL) is added dropwise to a solution of 5-aminopyrazine-2-carbonitrile (1.20 g, 10 mmol) and pyridine (2 mL) in CH$_2$Cl$_2$ (200 mL) and THF (25 mL) at room temperature. The reaction mixture is stirred at room temperature for 3 hours. The mixture is concentrated and the crude product is diluted with ethyl acetate, filtered, and concentrated to give the title compound.

Preparation 2

(tert-Butyl 3-(2-acetyl-3-methoxyphenoxy)propylcarbamate

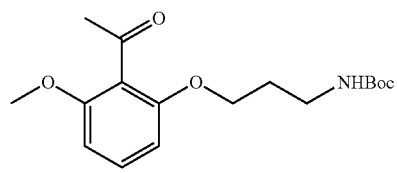 [SMILES: COc1cccc(OCCCNC(=O)OC(C)(C)C)c1C(C)=O]

DIAD (2.82 g, 14.0 mmol) is added to a stirred solution of tert-butyl 3-hydroxypropylcarbamate (2.45 g, 14.0 mmol), 1-(2-hydroxy-6-methoxyphenyl)ethanone (1.94 g, 11.7 mmol) and triphenylphosphine (3.66 g, 14.0 mmol) in THF (50 mL) at room temperature. After stirring for 18 hours, the solvent is removed under reduced pressure and the crude product is chromatographed (hexanes-ethyl acetate: 0-60% gradient) to afford the title compound (1.60 g, 42%).

EXAMPLE 1

5-(5-(2-(3-Aminopropoxy)-6-methoxyphenyl)-1H-pyrazol-3-ylamino)pyrazine-2-carbonitrile formic acid salt

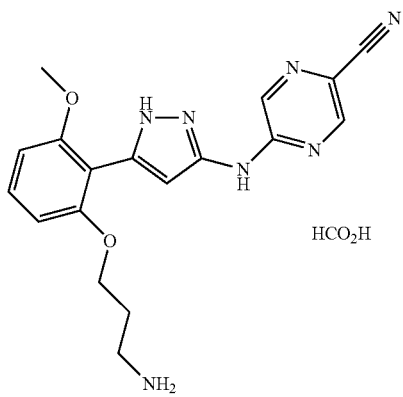 [SMILES: COc1cccc(OCCCN)c1-c1cc(Nc2cnc(C#N)cn2)n[nH]1 ; "HCO2H"]

A 1 M solution of lithium hexamethyl disilazane in THF (7.6 mL, 7.6 mmol) is added slowly to a stirred solution of tert-butyl 3-(2-acetyl-3-methoxyphenoxy)propylcarbamate (1.08 g, 3.17 mmol) in dry THF (25 mL) at room temperature. After stirring for 10 minutes, 5-isothiocyanatopyrazine-2-carbonitrile (0.510 g, 3.17 mmol) in THF (4 mL) is added and stirring is continued for 30 minutes. The reaction mixture is concentrated, and redissolved in EtOH (50 mL) and acetic acid (5 mL), followed by the addition of hydrazine hydrate (2 mL). The resulting reaction mixture is then heated to 120° C. for 2 minutes. The reaction mixture is then cooled to room temperature, diluted with water (100 mL), and extracted with ethyl acetate (2×100 mL). The organic portion is dried over anhydrous Na$_2$SO$_4$, filtered, and concentrated. The crude product is redissolved in CH$_2$Cl$_2$ (50 mL), treated with trifluoroacetic acid (10 mL) and stirred at room temperature for 15 minutes. The solvent is removed and the crude product (1.20 g) is purified using preparative HPLC to afford the title compound (0.046 g, 3.5%). LC-ES/MS m/z 366.1 [M+H]$^+$.

Route B

Preparation 3

1-[2-Methoxy-6-(4-methoxybenzyloxy)phenyl]ethanone

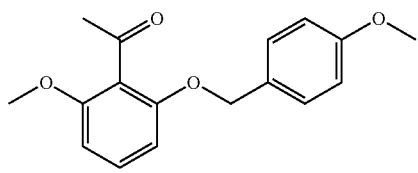

A flask is charged with 1-(2-hydroxy-6-methoxyphenyl)ethanone (30 g, 180.5 mmol), potassium carbonate, (49.9 g, 361 mmol), sodium iodide (2.68 g, 18.1 mmol), and 4-methoxybenzylchloride (27.0 mL, 198.6 mmol) in THF and the mixture is heated to reflux overnight. The mixture is cooled to room temperature, diluted with water, and extracted with ethyl acetate. The combined organic extracts are washed with brine and dried over anhydrous MgSO$_4$, filtered, and concentrated. The crude product is purified by silica gel chromatography with an eluent of ethyl acetate/hexanes to give the title product (32.51 g, 57%) as a white solid.

Preparation 4

1-(2-Methoxy-6-(4-methoxybenzyloxy)phenyl)-3,3-bis(methylthio)prop-2-en-1-one

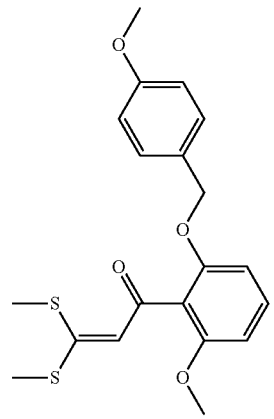 [SMILES: COc1ccc(COc2cccc(OC)c2C(=O)C=C(SC)SC)cc1]

A 500 mL round bottom flask is charged with 95% NaH (7.28 g, 288 mmol) and dry DMSO is added (170 mL). To the resulting heterogeneous mixture is added dropwise, 1-[2-methoxy-6-(4-methoxybenzyloxy)phenyl]ethanone (41.2 g, 144 mmol) in dry DMSO (60 mL). The mixture is stirred at room temperature for 10 minutes, at which time carbon disulfide is added dropwise (8.69 mL, 144 mmol), followed immediately by methyl iodide (18.0 mL, 288 mmol). Heat and gas are evolved during the addition of both reagents prompting careful addition. The homogenous solution is stirred for 18 hours at room temperature and then poured slowly into three volumes of water. The solid product is filtered and dried under high vacuum to give the title compound as an orange solid.

Preparation 5

5-Bromo-N-(5-(2-methoxy-6-(4-methoxybenzyloxy)phenyl)-1H-pyrazol-3-yl)pyrazin-2-amine

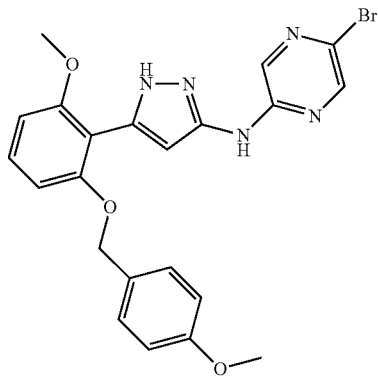 [SMILES: COc1ccc(COc2cccc(OC)c2-c2cc(Nc3cnc(Br)cn3)n[nH]2)cc1]

5-Bromopyrazin-2-amine (3.73 g, 21.4 mmol) is dissolved in THF (30 mL) and the mixture is cooled to −78° C. A solution of n-butyllithium in hexane (10.32 mL, 23.5 mmol) is added slowly. The reaction mixture is stirred at low temperature for 15 minutes and then warmed slowly to room temperature and stirred an additional one hour. The mixture is recooled to 0° C. and a solution of 1-(2-methoxy-6-(4-methoxybenzyloxy)phenyl)-3,3-bis(methylthio)prop-2-en-1-one (8.39 g, 21.4 mmol) in THF (50 mL) is added via cannula. The solution becomes homogenous and is stirred 15 minutes at room temperature before being heated to reflux for 10 hours. The solution is then cooled to room temperature and the solvent is removed under reduced pressure. The solid residue is dissolved in EtOH (150 mL) and glacial acetic acid (1.3 mL, 23.5 mmol) is added. Hydrazine hydrate (5.25 mL, 107 mmol) is added and the solution is refluxed an additional 8 hours. The mixture is cooled to room temperature and concentrated under vacuum. The product is purified by silica gel chromatography (CH$_2$Cl$_2$/MeOH) to give the title compound (5.76 g, 74%) as a brown solid.

Preparation 6

2-(3-(5-Bromopyrazin-2-ylamino)-1H-pyrazol-5-yl)-3-methoxyphenol

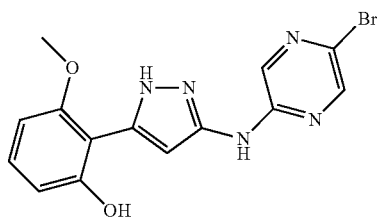 [SMILES: COc1cccc(O)c1-c1cc(Nc2cnc(Br)cn2)n[nH]1]

5-Bromo-N-(5-(2-methoxy-6-(4-methoxybenzyloxy)phenyl)-1H-pyrazol-3-yl)pyrazin-2-amine (3.1 g, 6.43 mmol) is dissolved in MeOH (100 mL). HCl gas is bubbled through the reaction mixture for 20 minutes. The mixture is stirred for 2 hours and the solvent is removed under reduced pressure. The residue is redissolved in 3:1 chloroform/isopropanol (100 mL) and combined with saturated NaHCO$_3$ solution (100 mL). The layers are separated and the aqueous layer is extracted with ethyl acetate (3×50 mL). The combined organic layers are concentrated and triturated with MeOH to give the title compound (1.5 g, 64%) as a brown solid.

Preparation 7 tert-Butyl 3-(2-(3-(5-bromopyrazin-2-ylamino)-1H-pyrazol-5-yl)-3-methoxyphenoxy)propylcarbamate

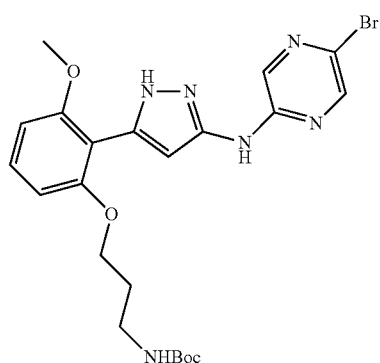 [SMILES: COc1cccc(OCCCNC(=O)OC(C)(C)C)c1-c1cc(Nc2cnc(Br)cn2)n[nH]1]

DIAD (1.73 mL, 8.76 mmol) is added to a stirred solution of tert-butyl 3-hydroxypropylcarbamate (0.83 mL, 4.83 mmol), 2-(3-(5-bromopyrazin-2-ylamino)-1H-pyrazol-5-yl)-3-methoxyphenol (1.59 g, 4.38 mmol) and polystyrene triphenylphosphine (5.91 g, 8.76 mmol) in THF (50 mL) at room temperature. After stirring for 45 minutes, the reaction is filtered, and the solvent is removed under reduced pressure. The resulting residue is chromatographed (MeOH/CH$_2$Cl$_2$) to afford the title compound (1.27 g, 54%) as a yellow solid.

Preparation 8 tert-Butyl 3-(2-(3-(5-cyanopyrazin-2-ylamino)-1H-pyrazol-5-yl)-3-methoxyphenoxy)propylcarbamate

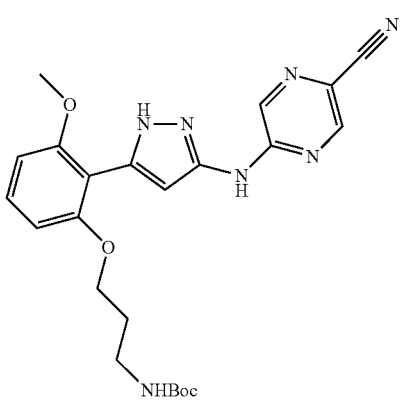 [SMILES: COc1cccc(OCCCNC(=O)OC(C)(C)C)c1-c1cc(Nc2cnc(C#N)cn2)n[nH]1]

A solution of tert-butyl 3-(2-(3-(5-bromopyrazin-2-ylamino)-1H-pyrazol-5-yl)-3-methoxyphenoxy)propylcarbamate (0.378 g, 0.730 mmol) and zinc cyanide (0.10 g, 0.870 mmol) in DMF (10 mL) is degassed with a stream of nitrogen for one hour and then heated to 80° C. To the reaction is added Pd(Ph₃P)₄ (0.080 g, 0.070 mmol), and the mixture is heated overnight. The reaction is cooled to room temperature and concentrated under reduced pressure. The residue is purified by silica gel chromatography (CH$_2$Cl$_2$/MeOH) to give the title compound (0.251 g, 73%).

Route C

Preparation 9

(E)-5-(3-(2-Methoxy-6-(4-methoxybenzyloxy)phenyl)-1-(methylthio)-3-oxoprop-1-enylamino)pyrazine-2-carbonitrile

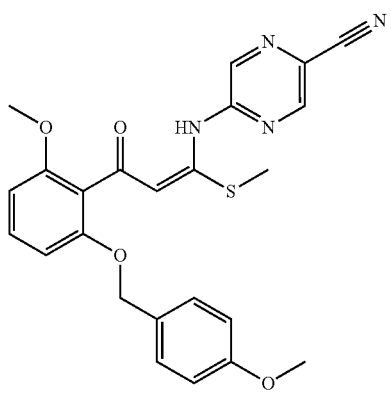 [SMILES: COc1ccc(COc2cccc(OC)c2C(=O)/C=C(\Nc2cnc(C#N)cn2)SC)cc1]

A 5 liter flange-neck flask equipped with an air stirrer rod and paddle, thermometer, water condenser and nitrogen bubbler is charged with sodium hydride (22.4 g, 560.1 mmol) and anhydrous THF (3 L). To the well stirred mixture is added 2-amino-5-cyanopyrazine (67.0 g, 557.8 mmol) portion-wise over 1.5 hours while allowing for any foaming. The internal temperature remains at 22° C. throughout. The mixture is stirred for 35 minutes. Then 1-(2-methoxy-6-(4-methoxy-benzyloxy)-phenyl)-3,3-bis-methylsulfanyl-propenone (146.0 g, 373.9 mmol) is added at 22° C. over one hour. The yellow suspension is stirred for 45 minutes at room temperature and then heating is applied until the reaction is at a gentle reflux. After 19 hours at 65° C. the reaction mixture is cooled to 15° C. The mixture is then split in two halves and each lot is quenched into water (2 L) and extracted with ethyl acetate (2×1 L). The organic extracts are combined and washed with brine, dried over anhydrous Na$_2$SO$_4$, filtered, and concentrated under reduced pressure at 40° C. to give the title compound (196 g, 100% crude) as a yellow/orange solid which is used in the next step without further purification. LC-ES/MS m/z 463.2 [M+H]$^+$.

Preparation 10

5-(5-(2-Methoxy-6-(4-methoxybenzyloxy)phenyl)-1H-pyrazol-3-ylamino)pyrazine-2-carbonitrile

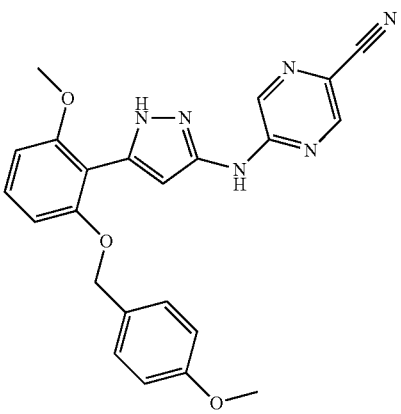 [SMILES: COc1ccc(COc2cccc(OC)c2-c2cc(Nc3cnc(C#N)cn3)n[nH]2)cc1]

A 10 L flange-neck flask, equipped with an air stirrer rod and paddle, thermometer, water condenser, and nitrogen bubbler, is charged with (E)-5-(3-(2-methoxy-6-(4-methoxybenzyloxy)phenyl)-1-(methylthio)-3-oxoprop-1-enylamino)pyrazine-2-carbonitrile (196 g, 423.8 mmol) and absolute EtOH (3 L). To the stirred suspension under nitrogen is added hydrazine hydrate (41.0 mL, 838.7 mmol) and glacial acetic acid (66.0 mL, 1.15 moles). A small exotherm is noted. The yellow suspension is warmed to 65° C. Heating is then discontinued and the reaction mixture is allowed to cool to room temperature. The mixture is allowed to stand overnight under a nitrogen atmosphere. The solid is collected by filtration, washed with fresh EtOH, and dried in vacuo at 45° C. to give the title compound (140 g, 87% yield for two steps) of a bright yellow solid. The product is used in the next step without further purification. LC-ES/MS m/z 429.2 [M+H]$^+$.

Preparation 11

5-(5-(2-Hydroxy-6-methoxyphenyl)-1H-pyrazol-3-ylamino)pyrazine-2-carbonitrile

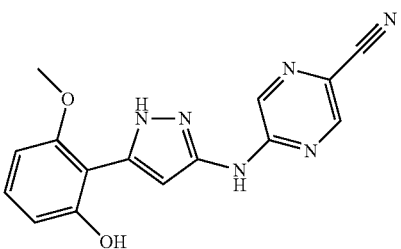 [SMILES: COc1cccc(O)c1-c1cc(Nc2cnc(C#N)cn2)n[nH]1]

A 10 L flange-neck flask equipped with an air stirrer rod and paddle, thermometer, water condenser, and outlet to caustic solution gas scrubbers is charged with 5-(5-(2-methoxy-6-(4-methoxybenzyloxy)phenyl)-1H-pyrazol-3-ylamino)pyrazine-2-carbonitrile (140 g, 326.76 mmol) and 4 N HCl (2500 mL, 10.0 mole) solution in 1,4-dioxane. The mixture is well stirred at 60-65° C. for 1.5 hours and allowed to cool to 50° C. After a total of 4 hours, more 4 N HCl in 1,4-dioxane is added (1000 mL) and heating to 65° C. resumed. After one hour at this temperature the heating is stopped and the mixture is allowed to cool to room temperature overnight with stirring. The mixture is filtered through a large sintered funnel. The solid collected is washed with fresh 1,4-dioxane and then pulled dry briefly. The bulk filter cake is returned to the 10 L flask and vigorously stirred with water (2 L) and ethyl acetate (3.5 L). The mixture is then made alkaline by adding concentrated ammonia (440 mL). The solution is filtered and then transferred to a 5 L separatory funnel. The aqueous layer is separated and extracted again with ethyl acetate (0.5 L). The combined organic layers are washed with brine, dried over sodium sulfate, filtered, and concentrated. The solid is dried in vacuo at 45° C. to give 101.3 g. The crude product is suspended in warm anhydrous THF (2.2 L) and loaded onto a pad of silica (1 kg) wet packed using iso-hexane. The product is eluted with ethyl acetate. The combined fractions are partially concentrated and the resulting precipitate is collected by filtration and dried in vacuo at 40° C. overnight to give the title compound (60.9 gm 60%). LC-ES/MS m/z 309.2 [M+1]$^+$.

Preparation 12 tert-Butyl 3-(2-(3-(5-cyanopyrazin-2-ylamino)-1H-pyrazol-5-yl)-3-methoxyphenoxy)propylcarbamate

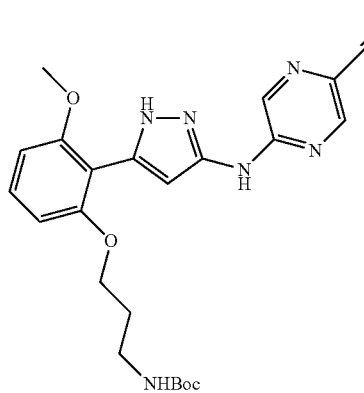

A 5 L flange-neck round-bottom flask equipped with an air stirrer rod and paddle, thermometer, pressure-equalizing dropping funnel, and nitrogen bubbler is charged with 5-(5-(2-hydroxy-6-methoxy-phenyl)-1H-pyrazol-3-ylamino)-pyrazine-2-carbonitrile (47.0 g, 152 mmol) and anhydrous THF (1.2 L). The stirred suspension, under nitrogen, is cooled to 0° C. A separate 2 L 3-necked round-bottom flask equipped with a large magnetic stirring bar, thermometer, and nitrogen bubbler is charged with triphenylphosphine (44.0 g; 168 mmol) and anhydrous THF (600 mL). The stirred solution, under nitrogen, is cooled to 0° C. and diisopropylazodicarboxylate (34.2 g; 169 mmol) is added and a milky solution is formed. After 3-4 minutes, a solution of t-butyl-N-(3-hydroxypropyl)-carbamate (30.3 g, 173 mmol) in anhydrous THF (100 mL) is added and the mixture is stirred for 3-4 minutes. This mixture is then added over 5 minutes to the stirred suspension of starting material at 0° C. The reaction mixture quickly becomes a dark solution and is allowed to slowly warm up to room temperature. After 6.5 hours, more reagents are prepared as above using PPh$_3$ (8 g), DIAD (6.2 g) and carbamate (5.4 g) in anhydrous THF (150 mL). The mixture is added to the reaction mixture, cooled to −5° C. and left to warm up to room temperature overnight. The solvent is removed in vacuo. The resulting viscous solution is loaded onto a pad of silica and the product is eluted with ethyl acetate. The concentrated fractions are separately triturated with MeOH and resulting solids are collected by filtration. The combined solids are triturated again with MeOH (400 mL) and then isolated by filtration and dried in vacuo at 50° C. overnight to give the title compound, (31.3 g, 44%). LC-ES/MS m/z 466.2 [M+1]$^+$.

EXAMPLE 2

5-(5-(2-(3-Aminopropoxy)-6-methoxyphenyl)-1H-pyrazol-3-ylamino)pyrazine-2-carbonitrile dihydrogen chloride salt

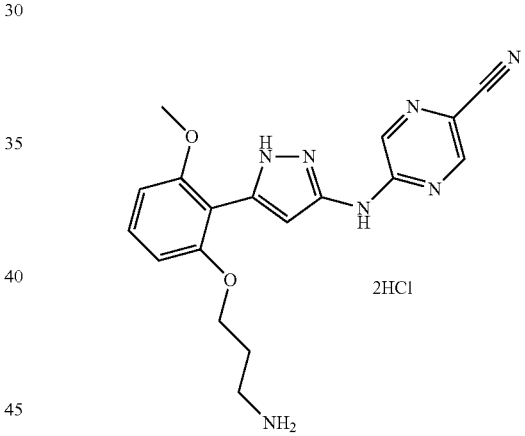

A 5 L flange-neck, round-bottom flask equipped with an air stirrer rod and paddle, thermometer, and air condenser with bubbler attached, is charged with tert-butyl 3-(2-(3-(5-cyanopyrazin-2-ylamino)-1H-pyrazol-5-yl)-3-methoxyphenoxy)propylcarbamate (30.9 g, 66.3 mmol) and ethyl acetate (3 L). The mechanically stirred yellow suspension is cooled to just below 10° C. Then hydrogen chloride from a lecture bottle is bubbled in vigorously through a gas inlet tube for 15 minutes with the ice-bath still in place. After 5 hours, the mixture is noticeably thickened in appearance. The solid is collected by filtration, washed with ethyl acetate, and then dried in vacuo at 60° C. overnight to give the title compound (30.0 g, 100%). $^1$H NMR (400 MHz, d$_6$-DMSO) δ 2.05 (m, 2H), 2.96 (m, 2H), 3.81 (s, 3H), 4.12 (t, J=5.8 Hz, 2H), 6.08 (br s, 3H), 6.777 (d, J=8.2 Hz, 1H), 6.782 (d, J=8.2 Hz, 1H), 6.88 (br s, 1H), 7.34 (t, J=8.2 Hz, 1H), 8.09 (br s, 1H), 8.55 (br s, 1H), 8.71 (s, 1H), 10.83 (s, 1H), 12.43 (br s, 1H). LC-ES/MS m/z 366.2 [M+1]$^+$.

EXAMPLE 3

5-(5-(2-(3-Aminopropoxy)-6-methoxyphenyl)-1H-pyrazol-3-ylamino)pyrazine-2-carbonitrile

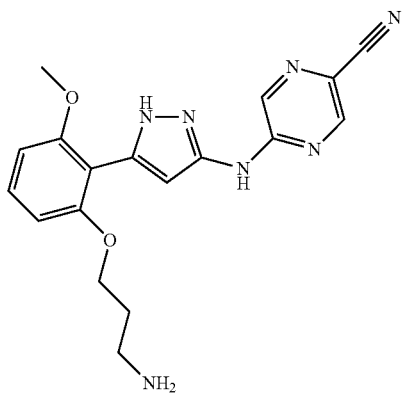 [SMILES: COc1cccc(OCCCN)c1-c1cc(Nc2cnc(C#N)cn2)n[nH]1]

5-(5-(2-(3-Aminopropoxy)-6-methoxyphenyl)-1H-pyrazol-3-ylamino)pyrazine-2-carbonitrile dihydrogen chloride salt (3.0 g, 6.84 mmol) is suspended in CH$_2$Cl$_2$ (200 mL). 1 N NaOH is added (200 mL, 200 mmol). The mixture is magnetically stirred under nitrogen at room temperature for 5 hours. The solid is collected by filtration and washed thoroughly with water. The filter cake is dried in vacuo at 50° C. overnight to give (2.26 g, 90%) of the free base as a yellow solid. $^1$H NMR (400 MHz, d$_6$-DMSO) δ 1.81 (m, 2H), 2.73 (t, J=6.2 Hz, 2H), 3.82 (s, 3H), 4.09 (t, J=6.2 Hz, 2H), 6.76 (t, J=8.2 Hz, 2H), 6.93 (br s, 1H), 7.31 (t, J=8.2 Hz, 1H), 8.52 (br s, 1H), 8.67 (s, 1H). LC-MS/ES m/z 366.2 [M+1]$^+$.

EXAMPLE 4

5-(5-(2-(3-Aminopropoxy)-6-methoxyphenyl)-1H-pyrazol-3-ylamino)pyrazine-2-carbonitrile methanesulfonic acid salt

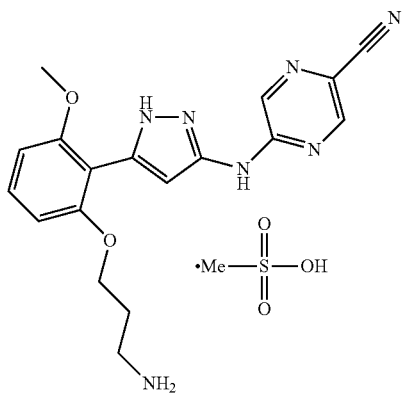

5-(5-(2-(3-Aminopropoxy)-6-methoxyphenyl)-1H-pyrazol-3-ylamino)pyrazine-2-carbonitrile (1.0 g, 2.74 mmol) is suspended in MeOH (100 mL). A 1 M solution of methanesulfonic acid in MeOH (2.74 mL, 2.74 mmol) is added to the mixture dropwise with stirring. The solid nearly completely dissolves and is sonicated and stirred for 15 minutes, filtered, and concentrated to 50 mL. The solution is cooled overnight at −15° C. and the solid that forms is collected by filtration. The solid is dried in a vacuum oven overnight to give (0.938 g, 74%) of a yellow solid. $^1$H NMR (400 MHz, d$_6$-DMSO) δ 1.97 (m, 2H), 2.28 (s, 3H), 2.95 (m, 2H), 3.79 (s, 3H), 4.09 (t, J=5.9 Hz, 2H), 6.753 (d, J=8.4 Hz, 1H), 6.766 (d, J=8.4 Hz, 1H), 6.85 (br s, 1H), 7.33 (t, J=8.4 Hz, 1H), 7.67 (br s, 3H), 8.49 (br s, 1H), 8.64 (s, 1H), 10.70 (s, 1H), 12.31 (s, 1H). LC-ES/MS m/z 366.2 [M+1]$^+$.

Route D

Preparation 13

1-[2-Methoxy-6-(4-methoxybenzyloxy)phenyl]ethanone

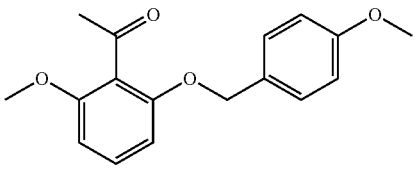

1-(2-Hydroxy-6-methoxyphenyl)ethanone (1300 g, 7.82 mol) and DMF (10.4 L) are added to a 22 L flask and stirred to obtain a solution. Potassium carbonate (2700 g, 19.54 mol) is added in portions and the mixture is stirred for at least 30 minutes. Using an addition funnel, 4-methoxybenzyl chloride (14700 g, 9.39 mol) is added dropwise over 2.5 hours to the mixture while maintaining the temperature<30° C. The reaction mixture is warmed to 35° C. and the reaction is held at that temperature for 12 hours. The reaction conversion is monitored by HPLC and deemed complete after 13 hours at 35° C. The slurry is filtered and the resulting solids washed with DMF (1 L). Extractive work-up of the filtrate with ethyl acetate and water, followed by concentration, provides a waxy yellow solid. To the waxy yellow solid is added methyl t-butyl ether (2.6 L). The resulting slurry is agitated. The now free flowing slurry is filtered and washed with methyl t-butyl ether (1 L). The white solid is vacuum dried to give the title compound (1539 grams, 69%) of the title compound. mp 105-107° C.

Preparation 14

1-(2-Methoxy-6-(4-methoxybenzyloxy)phenyl)-3,3-bis(methylthio)prop-2-en-1-one

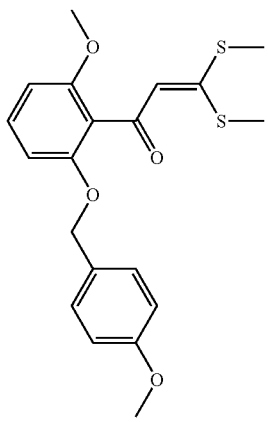 [SMILES: COc1ccc(COc2cccc(OC)c2C(=O)C=C(SC)SC)cc1]

To a mixture of lithium tert-butoxide (602.4 g, 7.52 mol) in anhydrous DMSO (11.0 L) under a nitrogen atmosphere is added 1-(2-methoxy-6-(4-methoxybenzyloxy)phenyl) ethanone (1000.0 g, 3.49 mol). The resulting mixture is stirred 30 minutes and $CS_2$ (259 mL, 4.296 mol) is slowly added over 1 to 1.5 hours while maintaining the internal temperature below 30° C. After stirring for at least one hour at ambient temperature, iodomethane (1000 g, 7.045 mol) is added slowly while maintaining the internal temperature below 30° C. The resulting mixture is stirred at ambient temperature for 30 minutes to one hour. Reaction completion is confirmed by HPLC. The resulting reaction mixture is cooled, followed by extractive work up with water and ethyl acetate. The resulting organic portion is concentrated to provide a slurry which is filtered and washed with ethyl acetate (1 L), followed by methyl t-butyl ether (2×1 L). The isolated solid is dried at 40° C. in a vacuum oven to provide the title compound (1057 g, 77%). mp 93-94° C.; ES/MS m/z 391.2 [M+1]$^+$.

Preparation 15

(E)-5-(3-(2-Methoxy-6-(4-methoxybenzyloxy)phenyl)-1-(methylthio)-3-oxoprop-1-enylamino)pyrazine-2-carbonitrile

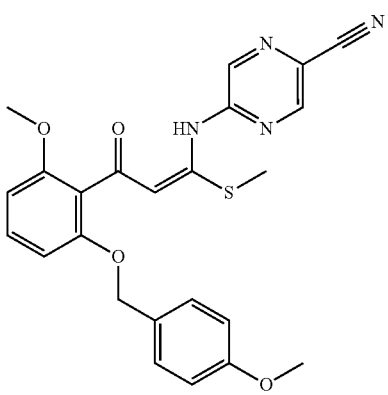 [SMILES: COc1ccc(COc2cccc(OC)c2C(=O)/C=C(\Nc2cnc(C#N)cn2)SC)cc1]

To a dry, inert 22 L flask is added sodium hydride (159.2 g, 3.98 mol) and THF (10.4 L). The mixture is cooled to 5-15° C. 5-Isocyanopyrazin-2-amine (382.2 g, 3.18 mol) is added in four portions over 30 minutes to control the release of hydrogen, allowing foaming to subside between additions and maintaining the temperature at 10° C. The mixture is stirred for 15-90 minutes while allowing the temperature to increase to 15° C. To the reaction mixture is added 1-(2-methoxy-6-(4-methoxybenzyloxy)phenyl)-3,3-bis(methylthio)prop-2-en-1-one (1036 g, 2.65 mol) in portions to control foaming. The resulting slurry is stirred for 15 minutes. The mixture is heated to a gentle reflux at 66° C. The reaction conversion is monitored by HPLC. The reaction mixture is quenched into chilled water (14.2 L) followed by extractive work up with ethyl acetate. The organic portion is concentrated to form a slurry which is filtered to provide the title compound (957 g, 78%). mp 128-135° C.; ES/MS m/z 463.2 [M+1]$^+$.

Preparation 16

5-(5-(2-Methoxy-6-(4-methoxybenzyloxy)phenyl)-1H-pyrazol-3-ylamino)pyrazine-2-carbonitrile

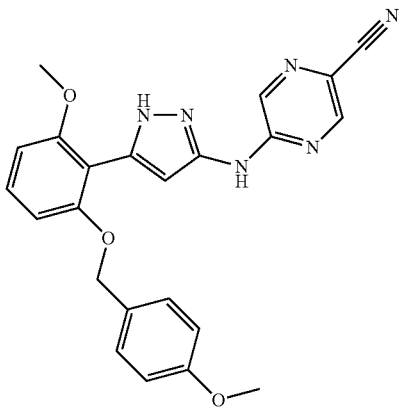 [SMILES: COc1ccc(COc2cccc(OC)c2-c2cc(Nc3cnc(C#N)cn3)n[nH]2)cc1]

EtOH (11.28 L) and acetic acid (318 mL, 5.545 mol) are combined. The reaction is vented to a bleach scrubber with a nitrogen purge. (E)-5-(3-(2-Methoxy-6-(4-methoxybenzyloxy)phenyl)-1-(methylthio)-3-oxoprop-1-enylamino)pyrazine-2-carbonitrile (940 g, 1.931 mol) and the EtOH/acetic acid solution are added to a 22 L reaction flask. To the resulting brown slurry is added hydrazine monohydrate (197 g, 3.935 mol), resulting in a slight exotherm. The resulting yellow slurry is slowly heated to 65-70° C. and monitored by HPLC. The duration of the reaction is less than one hour. The thick slurry is slowly cooled over 1-2 hours to less than 30° C. The slurry is filtered and washed with cold EtOH. The material is vacuum dried at 40° C. to give the title compound (820 g, 99.1%). mp 215-117° C.; ES/MS m/z 429.2 [M+1]$^+$.

Preparation 17

5-(5-(2-Hydroxy-6-methoxyphenyl)-1H-pyrazol-3-ylamino)pyrazine-2-carbonitrile dihydrogen chloride salt

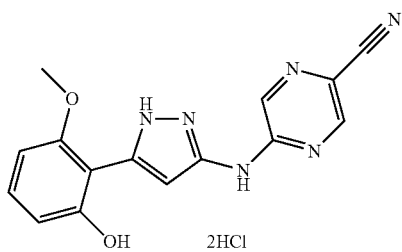 [SMILES: COc1cccc(O)c1-c1cc(Nc2cnc(C#N)cn2)n[nH]1]

All operations below are vented to a caustic scrubber system to control the HCl gassing. 5-(5-(2-Methoxy-6-(4-methoxybenzyloxy)phenyl)-1H-pyrazol-3-ylamino)pyrazine-2-carbonitrile (1.24 kg, 2.89 mol) and 4 N HCl in dioxane (26.06 kg, 99.28 mol) are charged to a 60 L glass reactor. The slurry is slowly heated to 60-70° C. The reaction is monitored by HPLC. After 9 hours, the reaction is determined to be complete. The brown slurry is cooled to 20° C. and held overnight. The acidic reaction mixture is filtered and the cake is washed with ethyl acetate (7 L). The wet cake is vacuum dried to a constant weight to provide the title compound (1010 g, 91.84% corrected yield). mp 225-228° C. (free base); ES/MS m/z 309.2 [M+1]⁺.

Preparation 18 tert-Butyl 3-(2-(3-(5-cyanopyrazin-2-ylamino)-1H-pyrazol-5-yl)-3-methoxyphenoxy)propylcarbamate

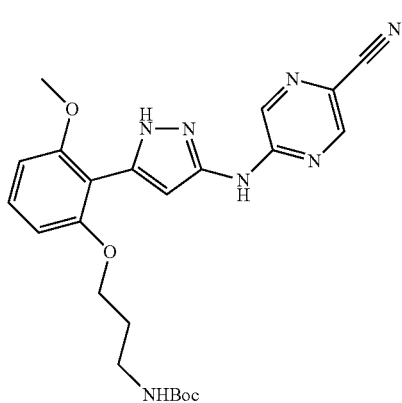 [SMILES: COc1cccc(OCCCNC(=O)OC(C)(C)C)c1-c1cc(Nc2cnc(C#N)cn2)n[nH]1]

5-(5-(2-Hydroxy-6-methoxyphenyl)-1H-pyrazol-3-ylamino)pyrazine-2-carbonitrile (618 g, 1.62 mol) is slurried in THF (6.18 L, 10 volumes) and chilled to −5 to 0° C. with an acetone/ice bath. Triethylamine (330 g, 3.25 mol) is added through an addition funnel over 30-40 min at −5 to 5° C. The resulting slurry is stirred at −5 to 5° C. for 60-90 minutes. The insoluble triethylamine hydrochloride is filtered and the solution of the phenol ((5-(2-hydroxy-6-methoxyphenyl)-1H-pyrazol-3-ylamino)pyrazine-2-carbonitrile) is collected in an appropriate reaction vessel. The cake is rinsed with THF (1.24 L). The THF solution of the phenol is held at 15 to 20° C. until needed. Triphenylphosphine (1074 g, 4.05 mol) is dissolved at room temperature in THF (4.33 L). The clear colorless solution is cooled with an acetone/ice bath to −5 to 5° C. Diisopropylazodicarboxylate (795 g, 3.89 mol) is added dropwise through an addition funnel over 40-60 minutes, keeping the temperature below 10° C. The resulting thick white slurry is cooled back to −5 to 0° C. tert-Butyl 3-hydroxypropylcarbamate (717 g, 4.05 moles) is dissolved in a minimum of THF (800 mL). The tert-butyl 3-hydroxypropylcarbamate/THF solution is added through an addition funnel, over 20-30 minutes at −5 to 5° C. to the reagent slurry. The prepared reagent is stirred in the ice bath at −5 to 0° C. until ready for use.

The prepared reagent slurry (20%) is added to the substrate solution at 15 to 20° C. The remaining reagent is returned to the ice bath. The substrate solution is stirred at ambient temperature for 30 minutes and sampled for HPLC. A second approximately 20% portion of the reagent is added to the substrate, stirred at ambient and sampled as before. Addition of the reagent is continued with monitoring for reaction completion by HPLC. The completed reaction is concentrated and triturated with warm MeOH (4.33 L, 50-60° C.) followed by cooling in an ice bath. The resulting yellow precipitate is filtered, rinsed with cold MeOH (2 L), and dried to constant weight to provide the title compound (544 g, 72%) of the title compound. mp 214-216° C.; ES/MS m/z 466.2 [M+1]⁺.

EXAMPLE 5

5-(5-(2-(3-Aminopropoxy)-6-methoxyphenyl)-1H-pyrazol-3-ylamino)pyrazine-2-carbonitrile methanesulfonic acid monohydrate

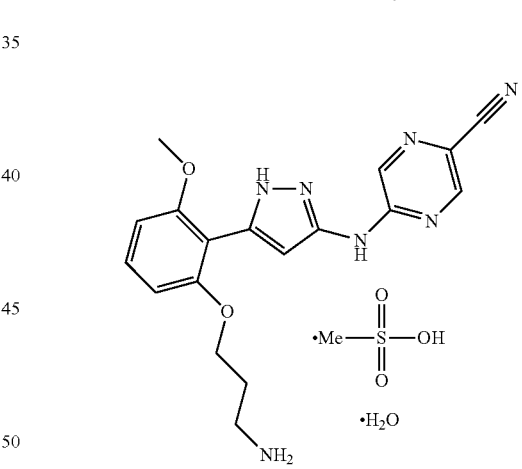

tert-Butyl 3-(2-(3-(5-cyanopyrazin-2-ylamino)-1H-pyrazol-5-yl)-3-methoxyphenoxy)propylcarbamate (1430 g, 3.07 mol) is slurried with acetone (21.5 L) in a 30 L reactor. Methanesulfonic acid (1484 g, 15.36 mol) is added through an addition funnel in a moderate stream. The slurry is warmed to reflux at about 52° C. for 1 to 3 hours and monitored for reaction completion by HPLC analysis. The completed reaction is cooled from reflux to 15 to 20° C. over 4.5 hours. The yellow slurry of 5-(5-(2-(3-aminopropoxy)-6-methoxyphenyl)-1H-pyrazol-3-ylamino)pyrazine-2-carbonitrile dimesylate salt is filtered, rinsed with acetone (7 L) and dried in a vacuum oven. The dimesylate salt, (1608 g, 2.88 mol) is slurried in water (16 L). Sodium hydroxide (aqueous 50%, 228 g, 2.85 mol) is slowly poured into the slurry. The slurry is heated to 60° C. and stirred for 1 hour.

It is then cooled to 16° C. over 4 hours and filtered. The wet filter cake is rinsed with acetone (4 L) and dried to constant weight in a vacuum oven at 40° C. to provide the title compound (833 g, 94%). mp 222.6° C.; ES/MS m/z 366.2 [M+1]$^+$.

Alternate Preparation, Example 5

5-(5-(2-(3-Aminopropoxy)-6-methoxyphenyl)-1H-pyrazol-3-ylamino)pyrazine-2-carbonitrile methanesulfonic acid monohydrate Crude 5-(5-(2-(3-aminopropoxy)-6-methoxyphenyl)-1H-pyrazol-3-ylamino)pyrazine-2-carbonitrile methanesulfonic acid monohydrate is purified using the following procedure. The technical grade 5-(5-(2-(3-aminopropoxy)-6-methoxyphenyl)-1H-pyrazol-3-ylamino)pyrazine-2-carbonitrile methanesulfonic acid monohydrate (1221 g, 2.55 mol) is slurried in a solvent mixture of 1:1 acetone/water (14.7 L). The solid is dissolved by warming the mixture to 50-55° C. The solution is polish filtrated while at 50-55° C. through a 0.22μ cartridge filter. The solution is slowly cooled to the seeding temperature of about 42-45° C. and seeded. Slow cooling is continued over the next 30-60 minutes to confirm nucleation. The thin slurry is cooled from 38 to 15° C. over 3 hours. A vacuum distillation is set up and the acetone removed at 110-90 mm and 20-30° C. The mixture is cooled from 30 to 15° C. over 14 hours, held at 15° C. for 2 hours, and then filtered. The recrystallized material is rinsed with 19:1 water/acetone (2 L) and then water (6 L) and dried to constant weight in a vacuum oven at 40° C. to provide the title compound (1024 g, 83.9%). mp 222.6° C.; ES/MS m/z 366.2 [M+1]$^+$.

X-ray powder diffraction (XRPD) patterns may be obtained on a Bruker D8 Advance powder diffractometer, equipped with a CuKα source (λ=1.54056 angstrom) operating at 40 kV and 40 mA with a position-sensitive detector. Each sample is scanned between 4° and 35° in °2θ±0.02 using a step size of 0.026° in 2θ±0.02 and a step time of 0.3 seconds, with a 0.6 mm divergence slit and a 10.39 mm detector slit. Primary and secondary Soller slits are each at 2°; antiscattering slit is 6.17 mm; the air scatter sink is in place.

TABLE 1

Characteristic peak positions and relative intensities of Example 5:

| Peak # | °2θ | Relative Intensity/Io |
|---|---|---|
| 1 | 8.42 | 22.8 |
| 2 | 12.64 | 85 |
| 3 | 13.16 | 36.7 |
| 4 | 16.86 | 43.7 |
| 5 | 21.05 | 44.4 |
| 6 | 21.25 | 64.3 |
| 7 | 21.63 | 42.6 |
| 8 | 24.11 | 40.6 |
| 9 | 24.69 | 30.1 |
| 10 | 25.02 | 43.1 |
| 11 | 25.4 | 30.3 |
| 12 | 26.15 | 100 |
| 13 | 29.24 | 26.2 |

Differential scanning calorimetry (DSC) analyses may be carried out on a Mettler-Toledo DSC unit (Model DSC822e). Samples are heated in closed aluminum pans with pinhole from 25 to 350° C. at 10° C./minute with a nitrogen purge of 50 mL/minute. Thermogravimetric analysis (TGA) may be carried out on a Mettler Toledo TGA unit (Model TGA/SDTA 851e). Samples are heated in sealed aluminum pans with a pinhole from 25 to 350° C. at 10° C./minute with a nitrogen purge of 50 mL/minute. The thermal profile from DSC shows a weak, broad endotherm form 80-140° C. followed by a sharp melting endotherm at 222° C., onset (225° C., peak). A mass loss of 4% is seen by the TGA from 25-140° C.

The results of the following assays demonstrate evidence that the compound, or a pharmaceutically acceptable salt thereof or a solvate of the salt, of the present invention is useful as a CHK1 inhibitor, CHK2 inhibitor, and as an anticancer agent. As used herein, "IC$_{50}$" refers to the concentration of an agent which produces 50% of the maximal inhibitory response possible for that agent and "EC$_{50}$" refers to the concentration of an agent which produces 50% of the maximal response possible for that agent.

CHK1 Biochemical Assay

The effect of compounds on CHK1 biochemical activity can be determined using a TR-FRET assay. In this assay, a terbium-labeled antibody is used to detect phosphorylated product formed from a reaction of kinase, fluorescein-labeled substrate, and ATP. The antibody binds to the phosphorylated substrate, resulting in an increase in the TR-FRET value calculated as the ratio of acceptor signal (fluorescein) to the donor signal (terbium).

The kinase reactions (25 μL reaction volumes) are performed in 96-well half-area black polystyrene plates (Costa, cat #3694). Reactions are initiated with the addition of ATP. Final reaction conditions are 50 mM HEPES pH 7.5, 0.005% (v/v) Triton™ X-100, 2 mM DTT, 2 mM MgCl$_2$, 104 nM fluorescein-PKC substrate (Invitrogen, cat #PV3506), 30 μM ATP, 1.5 nM active CHK1 enzyme (Millipore, cat #14-346), 4% (v/v) DMSO and serial dilution of the compound of Example 2 (1:3 serial dilution, starting at 20 μM, 10 points). Following ATP addition, the reactions are incubated at room temperature for 75 minutes, and then terminated with the addition of 25 μL of TR-FRET dilution buffer (Invitrogen #PV3574) containing 10 mM EDTA and 2.1 nM Tb-pSer antibody (Invitrogen, cat #PV3574). Quenched reactions are incubated at room temperature for 60 minutes, and then TR-FRET measured using an Envision plate reader from PerkinElmer with filters for Ex340 nm, Em495 nm and Em520 nm wavelength.

For IC$_{50}$ determination, the percent inhibition for each concentration is calculated using the TR-FRET ratio from controls run on each plate. The ten-point compound concentration data are subsequently fit to a four-parameter logistic equation using ActivityBase 4.0. Absolute IC$_{50}$ values are calculated from the resulting curve. The compound of Example 2 is measured in this assay to have an IC$_{50}$ of <0.001 μM. This demonstrates that the compounds of the present invention are potent inhibitors of CHK1.

CHK2 Biochemical Assay

The effect of compounds on CHK2 biochemical activity can be determined using a TR-FRET assay. In this assay, a terbium-labeled antibody is used to detect phosphorylated product formed from a reaction of kinase, fluorescein-labeled substrate, and ATP. The antibody binds to the phosphorylated substrate, resulting in an increase in the TR-FRET value calculated as the ratio of acceptor signal (fluorescein) to the donor signal (terbium).

The kinase reactions (25 μL reaction volumes) are performed in 96-well half-area black polystyrene plates (Costa, cat #3694). Reactions are initiated with the addition of ATP. Final reaction conditions are 50 mM HEPES pH 7.5, 0.005% (v/v) Triton™ X-100, 2 mM DTT, 2 mM MgCl$_2$, 104 nM fluorescein-PKC substrate (Invitrogen, cat #PV3506), 30 µM ATP, 2.5 nM active CHK2 enzyme (Millipore, cat #14-347), 4% (v/v) DMSO and serial dilution of the compound of Example 2 (1:3 serial dilution, starting at 20 µM, 10 points). Following ATP addition, the reactions are incubated at room temperature for 75 minutes, and then terminated with the addition of 25 µL of TR-FRET dilution buffer (Invitrogen #PV3574) containing 10 mM EDTA and 2.1 nM Tb-pSer antibody (Invitrogen, cat #PV3574). Quenched reactions are incubated at room temperature for 60 minutes, and then TR-FRET measured using an Envision plate reader from PerkinElmer with filters for Ex340 nm, Em495 nm, and Em520 nm wavelength.

For IC$_{50}$ determination, the percent inhibition for each concentration is calculated using the TR-FRET ratio from controls run on each plate. The ten-point compound concentration data are subsequently fit to a four-parameter logistic equation using ActivityBase 4.0. Absolute IC$_{50}$ values are calculated from the resulting curve. The compound of Example 2 is measured in this assay to have an IC$_{50}$ of 0.0047 µM. This demonstrates that the compounds of the present invention are potent inhibitors of CHK2.

CHK1 Autophosphorylation Cell Based Assay

An inhibitor of CHK1 will prevent the kinase activity of the protein from phosphorylating substrates in cells in which the DNA damage response has been activated. An easily detectable substrate for CHK1 is an autophosphorylation site on CHK1 itself, serine 296. The following immunoblot assay can be used to measure the amount of phosphorylation of serine 296 on CHK1 and indirectly the activity level of the CHK1 protein kinase. HeLa cells (purchased from ATCC) are cultured in MEM w/Earle's salts (Invitrogen) w/L-glutamine (Gibco™) supplemented with 10% (v/v) heat inactivated FBS (Gibco™), 1×MEM non-essential amino acids (Gibco™), 1× sodium pyruvate (Gibco™) and 1×10$^5$ cells plated in 600 µL of MEM culture media (above) per well of a 24 well cell culture plate. Cells are incubated for 24 hours at 37° C., 5% CO$_2$, and 95%-100% humidity. Sixteen µL of a 4 µM stock of doxorubicin (Sigma) in culture media are added to each appropriate well to make a final concentration of 100 nM doxorubicin. Plates are returned to the incubator for 24 additional hours prior to CHK1 inhibitor compound addition. Compounds are solubilized at 10 mM in 100% DMSO, then diluted to 2 mM in 40% (v/v) DMSO and then diluted to 100 µM with culture media plus 4% (v/v) DMSO. Subsequently serial dilutions of the compounds (1:3) are prepared over a 100 µM to 0.005 µM range. Sixty-six µL of compound stock is added to the appropriate wells in the plate to produce a final DMSO concentration of 0.4% (v/v) and a final compound concentration range between 1 µM and 0.0005 µM. The plates are returned to the incubator for an additional two hours and then removed for cell lysis and processing. The media is then removed from the plate, each well washed once with 0.5 ml of ice cold DPBS (Gibco™), all liquid removed and the plate is placed on ice for the remainder of the procedure. To each well is added 75 µL of ice cold lysis buffer, consisting of Cell Extraction Buffer (Invitrogen) containing phosphatase inhibitors (Sigma) and protease inhibitors (Roche Diagnostics). After 10 minutes each well is scraped and the lysate transferred into a 1.5 mL polypropylene microcentrifuge tube on ice. Each lysate is sonicated for 45 seconds with a plate cuphorn sonicator (Misonix) while suspended in a water/ice bath. Fifty µL of each sample is transferred into a 0.5 mL polypropylene microcentrifuge tube containing 25 µL of 4× Laemmli Sample Buffer (240 mM Tris-HCl, pH6.8, 40% glycerol, 0.05% bromophenol blue, 8% w/v SDS and 20% (v/v) beta-mercaptol ethanol), heated at 95° C. for 5 minutes and stored frozen at −80° C. The remaining lysate is used for determination of protein concentration (BCA™ protein assay kit, Thermo Scientific). Five µg of each cell lysate in sample buffer is applied to an E-Page 96 well gel (Invitrogen) and subjected to electrophoresis according to the manufacturer's instructions. Proteins are electrotransferred from the gel to Immobilon-P membrane (Millipore) according to procedures well understood in the art [Towbin et al., 1979]. The membrane is rinsed briefly with 10 mM Tris/HCl pH 8.0, 150 mM NaCl and 0.05% (v/v) Tween 20 (TBST) and soaked for one hour at 25° C. in TBST/5% (v/v) reconstituted Carnation® instant milk. The membrane is washed four times with TBST for five minutes, then soaked at 4° C. for 24 hours in TBST/5% (w/v) BSA with an appropriate dilution of rabbit anti-phosphoCHK1 (serine 296) (Cell Signaling). The membrane is washed four times with TBST for five minutes at 25° C. and then soaked at 25° C. for two hours in TBST/5% milk containing an appropriate dilution of donkey anti-rabbit IgG conjugated to HRP (Amersham) to detect autophosphorylated CHK1 protein. The membrane is washed again four times with TBST for five minutes at 25° C. Antigen-antibody-reporter conjugates immobilized on the membrane are detected with the Super Signal Western Femto HRP-detection reagent (Pierce) as recommended by the manufacturer using a chemiluminescent imager (Fujifilm). Phospho-CHK1(ser296) band intensities are calculated using "Total Lab" software (Nonlinear Dynamics). The percent inhibition of the doxorubicin induced CHK1 autophosphorylation is calculated by using the following formula: % inhibition=(sample phosphoCHK1 band intensity−no doxorubicin negative control phosphoCHK1 band intensity)/(doxorubicin positive control phosphoCHK1 band intensity−no doxorubicin negative control phosphoCHK1 band intensity)×100. The compound of Example 2 is measured in this assay to have an EC$_{50}$ of <0.0005 µM. This demonstrates that the compounds of the present invention are potent inhibitors of CHK1.

Doxorubicin-Induced G2M Checkpoint Abrogation HeLa Cell-Based Acumen Assay

An inhibitor of CHK1 will disable the G2M DNA damage checkpoint in p53-minus tumor cells treated with the topoisomerase II inhibitor, doxorubicin. A measurement of G2M checkpoint abrogation is the phosphorylation of histone H3 on serine 10 that occurs after cells traverse the G2M checkpoint and enter mitosis. The following high content imaging assay can be used to measure the phosphorylation of histone H3 in cells. HeLa cells (purchased from ATCC) are cultured in MEM Media (Gibco™) supplemented with 10% (v/v) FBS and plated at 2000 cells per well in poly D-lysine coated clear bottom black plates (BD Biocoat Cat #3504640), 100 µL volume per well. Plates are then incubated in a cell culture incubator for 18-24 hours (37° C., 5% CO$_2$ and 95% relative humidity). Following the initial incubation, 20 µL of Gibco™ MEM Media 10% FBS containing 625 nM doxorubicin are added to the appropriate wells of the plates resulting in a final concentration of 125 nM. The plates are returned to the incubator for 24 hours, sufficient to arrest the cells at the G2M checkpoint. The next day the cells are treated with the compound of Example 2. The compound of Example 2 is solubilized at 10 mM in 100% DMSO and then diluted to a 10× stock starting at 50 µM in 4% (v/v) DMSO-MEM. Subsequently serial dilutions of the compound (1:2) are prepared over a 50 µM to 0.39 µM range. Thirteen µL of compound stock is added to the appropriate wells in the plate to produce a final DMSO concentration of 0.4% and a final compound concentration range between 5 µM and 0.039 µM. The plates are returned to the incubator for an additional seven hours and then removed for fixation. Liquid is carefully removed from each well and 100 µL of PREFER™ fixative (Anatech LTD. Cat #414) is added. Plates are retained at room temperature for 20 minutes, the fixative removed, and the cells are then permeabilized by the addition of 100 µL/well of 0.1% (v/v) Triton® X 100 (Pierce Cat #28314) in DPBS (Gibco™ cat #14040) for 10 minutes. The solution is removed and the plate washed twice with 100 µL DPBS per well followed by the addition of 100 µL of DPBS containing 50 µg/mL RNAase (Sigma Cat #R-6513) for one hour at room temperature. The RNAase solution is removed and the cells stained for the presence of histone H3 phosphorylated on serine 10 (pHH3) by adding to each well 50 µL of RNAase solution containing a 1:500 dilution of rabbit anti-pHH3 (ser10) (UBI Cat #06-570) plus 1% (w/v) BSA (Gibco™ cat #15260). Plates are sealed and kept at 4° C. overnight. The primary antibody is removed by washing each plate twice with 100 µL DPBS per well and replaced with 50 µL of a 1:750 dilution of goat anti-rabbit IgG coupled to Alexa dye 488 (Invitrogen cat#A11008) in DPBS plus 1% (w/v) BSA. Plates are kept for one hour at room temperature covered with aluminum foil to protect from light. The plates are again washed twice with 100 µL per well DPBS and replaced with 100 µL of 15 nM PI (1:100 dilution with PBS from the original solution, Molecular Probes cat #P3566). The plates are sealed with a black seal to protect the plates from light. Plates are incubated for 30 minutes to stain nuclei. Plates are scanned with ACUMEN EXPLORER™ Laser-scanning fluorescence microplate cytometers using 488 nm excitation (TTP LABTECH LTC) to measure pHH3 and DNA content including 2 N, and 4 N. The pHH3 positive cells are identified by mean intensity at 519 nm from Alexa 488. Total intensity at 655-705 nm from PI/DNA is used to identify individual cells and subpopulations in cell cycle (2N cells, 4N cells). The final readout for each population is determined by normalizing to the % of total cells producing a final assay output of % pHH3, %2 N and %4 N. 100% activity is then determined by treating cells with the maximum concentration of an inhibitor control compound at 100 nM to determine the final % activity of each compound. 0% activity is based on no compound treatment. The Relative $EC_{50}$ is determined by using ACTIVITY BASE™, excel fit, curve fitting using a four parameter logistic fit, equation 205, to determine the % pHH3 relative to control max at 100%. The compound of Example 2 is measured in this assay to have an EC50 of 0.0105 µM. This demonstrates that the compounds of the present invention will disable the G2M DNA damage checkpoint.

$EC_{tfs}$(Two-Fold Sensitization) Assay

An inhibitor of CHK1 can potentiate the anti-proliferative activity of gemcitabine (or other cytotoxics) through abrogation of the intra-S phase checkpoint, resulting in sustained and increased DNA damage. The capacity for continued tumor cell proliferation after DNA damage can be analyzed by determining the ability of cells to replicate their DNA. This assay assesses the ability of cells to replicate their DNA after cells have had an opportunity to repair DNA damage. In this assay, cells are treated with gemcitabine, and then with the compound of Example 2. Following a recovery period, cells are assayed for the ability to incorporate radioactive thymidine into DNA during S phase. The $EC_{tfs}$ parameter is a measure of the concentration of a CHK1 inhibitor necessary to reduce by half the GI90 concentration of gemcitabine, measured in this assay in the absence of CHK1 inhibition. HT-29 cells (obtained from ATCC), are grown in RPMI 1640 plus (Gibco™) 10% (v/v) heat inactivated FBS. These cells are plated at $1.3 \times 10^3$ per well on Corning Costar 96-well tissue culture plates. After plating the cells, the tissue culture plates are held at room temperature for 45 minutes, before returning to 37° C. Plates are incubated for 24 hours prior to gemcitabine addition. Before gemcitabine addition, medium is removed from all wells and replaced with 150 µL per well of fresh RPMI medium. Gemcitabine stocks at 10 mM are prepared in PBS. Gemcitabine dilutions were prepared at 4× concentrations in RPMI medium and added to wells at 50 µL per well. The highest final concentration of gemcitabine used is 80 µM and dilutions proceed by four-fold steps. Two hours later, gemcitabine-containing medium is removed from the wells and replaced with 150 µL per well of fresh RPMI medium. The compound of Example 2 (10 mM in DMSO) is diluted first in DMSO to 2000× final concentrations, and then diluted 1:500 into RPMI medium to generate 4× stocks for addition to wells. The volume of addition is 50 µL. Compound dilutions proceed by two-fold steps, starting at 5000 nM. Twenty-four hours after addition of the compound of Example 2, the medium containing inhibitors is removed by aspiration and replaced with 200 µL per well of fresh RPMI medium. Seventy-two hours after removal of the compound of Example 2, tritiated thymidine labeling is initiated. $^3$H-thymidine (NET 027X001, PerkinElmer, specific activity 20 Ci/mmol) is diluted 1:20 in complete RPMI to yield a concentration of 0.05 mCi/mL. Twenty L of this solution is added to each well, yielding 1 µCi/well of $^3$H-thymidine. Cells are labeled for twenty-two hours. The medium containing $^3$H-thymidine is thoroughly removed from the wells. The plates are then frozen at −20° C., for several hours. To harvest the DNA containing incorporated $^3$H-thymidine, plates are thawed for several minutes, and then 120 µL per well of 0.1N NaOH is added to each well. Each plate is then incubated at 37° C., with slow mixing on a rotator, for 10 minutes. DNA is harvested with a Filtermate 196 Harvester (PerkinElmer) and collected on 96-well Unifilter GF/C plates (PerkinElmer #6005174). The wells of the tissue culture plate on which cells had been labeled are washed with water (5×). The Unifilter plate membranes are washed with an additional 4.5 mL per well (3×1.0 mL and finally a 1.5 mL wash). The Unifi is sealed with a Backseal adhesive sheet (PerkinElmer), and the 50 µL/well of MicroScint-20 (Perkin Elmer) is added. Each plate is then sealed with a Topseal clear adhesive sheet (PerkinElmer). Plates are counted on a Topcount scintillation counter (PerkinElmer), at 1 minute per well. $^3$H-thymidine counts per minute (cpm) are exported into Prism (GraphPad) for analysis and plotting. A gemcitabine dose response is determined for each concentration of the compound of Example 2. To do this, cpm is normalized, setting 100% incorporation as the mean cpm for the compound of Example 2 concentration in the absence of gemcitabine and no incorporation (100% inhibition) as cpm=0 (no counts per minute). For plotting the data in Prism, the gemcitabine concentrations are transformed to log values, and dose-response curves are fit by non-linear regression. Neither top nor bottom fits are constrained. The $EC_{tfs}$ value is 0.3 nM. Furthermore, 3 nM of the compound of Example 2 decreases the $EC_{50}$ of gemcitabine 7-fold from 37 nM to 5 nM in HT29 colon carcinoma cells. The action of the compound of Example 2 also increases the percentage of proliferation inhibition from 52 for gemcitabine to 73 for the combination. Alone, 3 nM of the compound of Example 2 has little effect on the proliferation of HT29 cells.

CHK1 In Vivo Target Inhibition Assay

Calu-6 cells (ATCC) are cultured in growth media (MEM with Earle's salts (Invitrogen) with L-glutamine (Gibco™) supplemented with 10% (v/v) heat inactivated FBS (Gibco™), 1×MEM non-essential amino acids (Gibco™), 1× sodium pyruvate (Gibco™)) and expanded. Cells are harvested and washed twice with phosphate buffered saline and $1 \times 10^6$ cells in growth media (without serum) are mixed with equal volume of BD Matrigel™ matrix (BD Bioscience, Franklin, N.J.), then injected subcutaneously into the flank of pre-irradiated (4.5 Gy) nude mice (athymic nude, from Harlan, Indianapolis, Ind.). At day 15 after implant (tumor size=150-200 mm³), gemcitabine formulated fresh in saline (Hospira, Lake Forest, Ill.) daily is administered to animals by intraperitoneal route at 150 mg/kg dose. Six hours later animals are administered the compound of Example 2 formulated in molar ratio methane sulfonic acid/20% Captisol (CYDEX, Overland Park, Kans.) by intravenous route varying dose from 15 mg/kg downward. Animals are sacrificed 2 hours post CHK1 inhibitor dose, tumors harvested and immediately processed in ice cold Cell Extraction buffer (Invitrogen Cat #FNN0011) containing phosphatase inhibitors (Sigma) and protease inhibitors (Roche Diagnostics). Tumors are processed in 1.5-2.0 mL of lysis buffer in an iced 15 mL polypropylene conical tube using a motorized tissue homogenizer (Powergen 700) set to high for 15 seconds. With the sample kept on ice, the lysate is drawn four times through a 1 mL syringe with a 25 gauge needle. Next, 0.35 mL of tumor lysate is transferred into a 1.5 mL polypropylene microcentrifuge tube containing 0.15 mL of 4× Laemmli sample buffer (240 mM Tris-HCl, pH 6.8, 40% glycerol, 0.05% bromophenol blue, 8% w/v SDS and 20% (v/v) beta-mercaptol ethanol). Sample is then mixed and heated for 5 minutes at 95° C. and sonicated for one minute using high power on a Misonix 3000 plate horn sonicator. Samples are then stored on ice, or stored at −80° C. for target inhibition assessment by western blot. The remaining lysate is used for determination of protein concentration (BCA™ protein assay kit, Thermo Scientific). Five μg of each tumor lysate in sample buffer is applied to E-Page 96 well gels (Invitrogen) and subjected to electrophoresis according to the manufacturer's instructions. Proteins are transferred to Nitrocellulose Protran BA83 membrane (Whatman) according to procedures well understood in the art [Towbin et al., 1979]. The membrane is then processed to measure CHK1 protein autophosphorylated on serine 296. The membrane is rinsed briefly with water, then 10 mM Tris/HCl pH 8.0, 150 mM NaCl and 0.05% (v/v) Tween 20 (TBST) and soaked for one hour at 25° C. in TBST/5% (w/v) reconstituted Carnation® instant milk. The membrane is then washed four times with TBST for 5 minutes. The membrane is soaked at 4° C. for 16 hours in TBST/5% (w/v) BSA in an appropriate dilution of rabbit anti-phosphoCHK1 (serine 296) (Cell Signaling). Next, the membranes is washed four times with TBST for 5 minutes at 25° C. and then soaked at 25° C. for two hours in TBST/5% milk containing an appropriate dilution of donkey anti-rabbit IgG conjugated to HRP (Amersham) to detect phospho-CHK1(ser 296). The membrane is washed again 4 times with TBST for 5 minutes at 25° C. Antigen-antibody-reporter conjugates immobilized on the membrane are detected with the Super Signal Western Femto HRP-detection reagent (Pierce) as recommended by the manufacturer.

Signals are detected and captured using the FUJI LAS-4000 imaging system. Phospho-CHK1(ser296) band intensities are calculated using "Total Lab" software (Nonlinear Dynamics). The percent inhibition of the gemcitabine induced CHK1 autophosphorylation is calculated by using the following formula: % inhibition=(sample phosphoCHK1 band intensity−average gemcitabine (Max) positive control phosphoCHK1 band intensity)/(average negative control (Min) phosphoCHK1 band intensity−average gemcitabine (Max) positive control phosphoCHK1 band intensity)×100.

The compound of Example 2 is measured in this assay to have a Target Modulatory Effective Dose 50 (TMED50) for CHK1 autophosphorylation of 0.03 mg/kg.

Human Tumor Xenograft Models

The ability of CHK1 inhibitors to effect tumor killing can be determined in vivo using the Calu-6 lung and HT-29 colon tumor xenograft efficacy models. Calu-6 lung cancer cells (ATCC) are cultured in growth media (MEM w/Earle's salts (Invitrogen) with L-glutamine (Gibco™) supplemented with 10% (v/v) heat inactivated FBS (Gibco™), 1×MEM non-essential amino acids (Gibco™), 1× sodium pyruvate (Gibco®)) and HT-29 colon cancer cells (ATCC) are cultured in growth media, (McCoy's 5A medium (Gibco™) supplemented with 10% FBS (Gibco™)) and expanded. Cells are harvested and washed twice with phosphate buffered saline and $5 \times 10^6$ cells (HT-29) or $1 \times 10^6$ cells (Calu-6) in growth media (without serum) are mixed with equal volume of BD Matrigel™ matrix (BD Bioscience, Franklin, N.J.), then injected subcutaneously into the flank of nude mice (CD-1 nu/nu, from Charles River Labs, Wilmington, Mass.). At about day 16 after implant (150-200 mm³), gemcitabine is formulated fresh in saline daily and administered to animals by intraperitoneal route at 60 mg/kg dose. Twenty four hours later animals are administered the compound of Example 2, formulated in molar ratio methane sulfonic acid/20% Captisol (CYDEX, Overland Park, Kans.) by intravenous route. After a day of rest, dosing is repeated for 3 more cycles (Q3D×4 with CHK1 inhibitor offset +24 hours). Each dose group consists of nine animals. Tumor response is determined by tumor volume measurement performed twice a week during the course of treatment. Tumor growth inhibition (TGI) is calculated as the percent reduction in mean tumor size of a compound treated group from the mean tumor size of the vehicle-treated control group. The compound of Example 2 dosed alone and in combination with gemcitabine demonstrates excellent dose dependent anti-tumor activity in both the HT-29 and Calu-6 tumor xenograft models, with up to a six-fold increase in tumor growth inhibition over gemcitabine alone.

Single Agent Efficacy Dosing

The ability of CHK1 inhibitors to effect tumor killing can be determined in vivo using the Calu-6 lung xenograft efficacy model. Calu-6 lung cancer cells (ATCC) are cultured as described above. Cells are harvested and washed twice with phosphate buffered saline and $1 \times 10^6$ cells (Calu-6) in growth media (without serum) are mixed with equal volume of BD Matrigel™ matrix (BD Bioscience, Franklin, N.J.), then injected subcutaneously into the flank of nude mice (CD-1 nu/nu, from Charles River Labs, Wilmington, Mass.). At about day 16 after implant (150-200 mm³), the compound of Example 2 is dosed at 15 mg/kg (subcutaneously (SC), bi-daily (BID×5 rest 2 days)×3 cycles. Tumor response is determined by tumor volume measurement performed twice a week during the course of treatment. The compound of Example 2 dosed on the 5 day BID schedule (15 mg/kg) provides superior growth inhibition to the gemcitabine plus the compound of Example 2 combination schedule previously described. Complete tumor regression is rapid and durable.

Monolayer Proliferation and Cytotoxicity Assay

One measure of potency of a CHK1 inhibitor is its ability to inhibit the proliferation of cancer cells in culture due to uncontrolled replication origin activation. (Conti et al. *Cell Cycle* 6: 2760-2767, 2007) Determination of CHK1 inhibitor antiproliferative activity in cell lines derived from a broad range of tumor types is indicative of which tumor types may be clinically responsive to chemotherapy with CHK1 inhibitors. The following described cellular proliferation assay is run at Oncotest, GmbH in Germany. Thirty solid tumor cell lines are derived from 13 different tumor histotypes, each represented by 1 to 6 different cell lines (Oncotest, GmbH). They are established from cancer of the bladder, brain, colon, stomach, liver, lung, breast, ovary, pancreas, kidney and the uteri body, as well as from melanoma and pleuramesothelioma. All cell lines are established at Oncotest from patient-derived tumor xenografts (Roth et al. 1999). The origin of the donor xenografts is described by Fiebig et al. (Fieberg et al. 1992 and 1999). Cell lines are routinely passaged once or twice weekly and maintained in culture for up to 20 passages. All cells are grown at 37° C. in a humidified atmosphere with 5% $CO_2$ in RPMI 1640 medium (PAA, Cölbe, Germany) supplemented with 10% (v/v) fetal calf serum (PAA, Cölbe, Germany) and 0.1 mg/mL gentamicin (PAA, Cölbe, Germany). A modified PI assay is used to assess the cytotoxic activity of compounds against these cell lines. Briefly, adherent cells are harvested from exponential phase cultures by trypsinization, counted and plated in 96 well flat-bottomed microtiter plates at a cell density depending on the cell line (4.000-20.000 cells/well). After a 24 hour recovery period to allow the cells to adhere and to resume exponential growth, 10 µL of culture medium (6 control wells/plate) or of culture medium containing the compound of Example 2 is added. Stock solutions of the compound of Example 2 are prepared in DMSO at a concentration of 1 mM. Subsequent dilutions are done with complete RPMI 1640 cell culture medium as follows: the DMSO stock solution is first diluted 1:22 (containing 4.5% (v/v) DMSO). Using this solution, serial dilutions (half-log or 2-fold) in cell culture medium are made. For the final dilution step (1:15), 10 µL/well of the respective final compound solution is directly added to 140 µL/J well culture medium. The final DMSO concentration is ≤0.3% (v/v). The compound of Example 2 is applied in triplicates in a ten point concentration curve and treatment continued for 4 days. After 4 days of treatment, the culture medium is removed and replaced by 200 µL of an aqueous 7 µg/mL PI solution. To measure the number of vital cells, cells are permeabilized by freezing, resulting in the death of all cells that had remained attached to the well after the treatment with compound. Finally, PI fluorescence is measured using the Cytofluor 4000 microplate reader (excitation λ=530 nm, emission λ=620 nm) to determine the total viable cell number. Growth inhibition is expressed as Test/Control×100 (% T/C) values. Based on the T/C values, relative $IC_{50}$ values are determined using non-linear regression (log [conc. of inhibitor] versus response (% T/C)). The compound of Example 2 inhibits the growth of the majority of these tumor cell lines with an $EC_{50}$ under 20 nM.

In Vitro Response of Pediatric Cell Lines to 5-(5-(2-(3-Aminopropoxy)-6-methoxyphenyl)-1H-pyrazol-3-ylamino)pyrazine-2-carbonitrile methanesulfonic acid monohydrate Cellular lysates can be obtained from embryonal and alveolar rhabdomyosarcoma (RD and SJCRH30, respectively), osteosarcoma (Saos-2), and Ewing's sarcoma (RD-ES) cell lines treated with 5-(5-(2-(3-aminopropoxy)-6-methoxyphenyl)-1H-pyrazol-3-ylamino)pyrazine-2-carbonitrile methanesulfonic acid monohydrate (Example 5) for 24 hours at 5 and 50 nM final concentration.

A western blot can be run using the cellular lysates described above. Analysis of said western blots indicates that CHK1 protein levels do not change when the cell lines are treated with 5-(5-(2-(3-aminopropoxy)-6-methoxyphenyl)-1H-pyrazol-3-ylamino)pyrazine-2-carbonitrile methanesulfonic acid monohydrate (Example 5) and that phospho-CHK1 (S345) levels increase with treatment. Higher levels of DNA damage can be observed with CHK1 inhibition. Accordingly, the levels of gammaH2AX, a signal for DNA damage, increase upon treatment with 5-(5-(2-(3-aminopropoxy)-6-methoxyphenyl)-1H-pyrazol-3-ylamino)pyrazine-2-carbonitrile methanesulfonic acid monohydrate (Example 5). The levels of phospho-ERK ½ (T202/Y204), which are known to increase following CHK1 inhibition, also increase in three out of four cell lines with the non-responding RD-ES cell line being the least sensitive of the four in vitro. These data are also supported by the increase in phospho-hnRNP-C levels, a marker for CHK1 inhibition that is also unaffected in the RD-ES cell line. The levels of phospho-AKT do not appear to change following treatment with 5-(5-(2-(3-aminopropoxy)-6-methoxyphenyl)-1H-pyrazol-3-ylamino)pyrazine-2-carbonitrile methanesulfonic acid monohydrate (Example 5).

Xenograft Tumor Models

The following protocol can be used to measure reductions in tumor volume in response to an active pharmaceutical ingredient. Expand human NBM cancer cells SH-SY5Y (ATCC, #CRL-2226) in culture, harvest, and inject 5×10⁶ cells in 200 µL of 1:1 solution of HBSS and Matrigel® subcutaneously into the right rear flank of female CD-1 nu/nu mice (20-24 g, Charles River Laboratories). Expand human NBM cancer cells KELLY (Sigma-#92110411) in culture, harvest, and inject 5×10⁶ cells in 200 µL of 1:1 solution of HBSS and Matrigel® subcutaneously into the right rear flank of female CB-17 SCID mice (20-24 g, Charles River Laboratories). Expand human NBM cancer cells IMR-32 (ATCC, #CCL-127) in culture, harvest, and inject 5×10⁶ cells in 200 µL of 1:1 solution of HBSS and Matrigel® subcutaneously into the right rear flank of female CB-17 SCID mice (20-24 g, Charles River Laboratories).

Expand human RMS cancer cells SJCRH-30 (St. Jude Children's Research Hospital) in culture, harvest, and inject 5×10⁶ cells in 200 µL of HBSS subcutaneously into the right rear flank of female athymic nude mice (20-22 g, Harlan Laboratories). Expand human rhabdomyosarcoma cancer cells RD (ATCC, #CCL-136) in culture, harvest, and inject, 5×10⁶ cells in 200 µL of HBSS subcutaneously into the right rear flank of female athymic nude mice (20-22 g, Harlan Laboratories).

For all "CTG" models (encompassing human RMS, DSRCT, EWS, OS and LMS patient-derived xenograft models), female NCr nude spontaneous mutant mice (5-8 weeks old, Taconic) are implanted unilaterally in the flank region with tumor fragments harvested from donor animals, each implanted from a specific passage lot.

For all "ST" models (encompassing RMS and LMS), patient-derived xenografts are established from viable human tumor tissue and are serially passaged in animals a limited number of times to maintain tumor heterogeneity. In subcutaneous models, athymic nude mice (Crl:NU(NCr)-Foxn1nu) or CB-17 SCID mice (CRL-CB17/Icr-Prkdcscid/IcrlcoCrl) are injected or implanted unilaterally into the flank with tumor fragments harvested from host animals, each implanted from a specific passage lot. For all studies, measure tumor growth and body weight twice per week beginning on the seventh day after implantation. When tumor size reaches 150-300 mm³, randomize animals and group into groups of 4-7 animals. Prepare test compound in an appropriate vehicle (e.g. vehicle can be 20% Captisol® in sterile water) and administer subcutaneously for three consecutive days followed by a four day dosing holiday and repeat for a minimum of four weeks. Tumor response is determined by tumor volume measurement performed twice per week during the course of treatment.

5-(5-(2-(3-Aminopropoxy)-6-methoxyphenyl)-1H-pyrazol-3-ylamino)pyrazine-2-carbonitrile methanesulfonic acid monohydrate (Example 5) is found to have % T/C or % regression values as provided in TABLE 2 below. These results indicate that 5-(5-(2-(3-aminopropoxy)-6-methoxyphenyl)-1H-pyrazol-3-ylamino)pyrazine-2-carbonitrile methanesulfonic acid monohydrate (Example 5) demonstrates significant anti-tumor activity in a range of human xenograft models including osteosarcoma (CTG-0242); Ewing's sarcoma (CTG-0994); DSRCT (CTG-0926); RMS (CTG-1213, CTG-1116, SJCRH-30 and ST162); and NBM (SH-SY5Y, KELLY, IMR-32); LMS (CTG-1006, ST1547).

TABLE 2

| Model Name | Histology | Comparator Day | % T/C[1] | % Regression | p-value | Note |
|---|---|---|---|---|---|---|
| CTG-0142 | EWS | 28 | 66 | NA | 0.376 | |
| CTG-0241 | OS | 28 | 48 | NA | 0.019 | |
| CTG-0242 | OS | 28 | 6 | NA | 0.012 | |
| CTG-0243 | OS | 22 | 43 | NA | 0.089 | |
| CTG-0785 | EWS | 18 | 57 | NA | 0.052 | |
| CTG-0816 | EWS | 28 | 44 | NA | 0.069 | |
| CTG-0926 | DSRCT | 28 | NA | −76 | <0.001 | |
| CTG-0994 | EWS | 25 | NA | −79 | <0.001 | |
| CTG-1064 | OS | 33 | NA | NA | 0.156 | |
| CTG-1213 | RMS | 36 | NA | −65 | <0.001 | |
| CTG-1213 | RMS | 18 | 18 | NA | 0.004 | |
| CTG-1116 | RMS | 17 | 8 | NA | <0.001 | |
| CTG-1006 | LMS | 27 | NA | −24 | <0.001 | |
| SH-SY5Y | NBM | 28 | NA | −21 | <0.001 | 8 mg/kg dose |
| KELLY | NBM | 49 | NA | −88 | <0.001 | |
| IMR-32 | NBM | 66 | NA | −72 | <0.001 | |
| SJCRH-30 | RMS | 38 | NA | −78 | <0.001 | |
| ST0001 | LMS | 19 | 292 | NA | 0.247 | |
| ST550 | LMS | 31 | 94 | NA | 0.712 | |
| ST240 | LMS | 29 | 67 | NA | 0.022 | |
| ST1547 | LMS | 28 | 5 | NA | <0.001 | |
| ST658 | LMS | 16 | 137 | NA | 0.592 | |
| ST162 | LMS | 39 | NA | −93 | <0.001 | |

[1]T/C refers to the treated to control value

Xenograft Tumor Models: Combination Studies

Combination therapy is a method of cancer treatment that can effectively block tumor growth and overcome acquired tumor resistance that often develops in response to single agents. 5-(5-(2-(3-Aminopropoxy)-6-methoxyphenyl)-1H-pyrazol-3-ylamino)pyrazine-2-carbonitrile methanesulfonic acid monohydrate (Example 5) can be tested in combination with a sarcoma standard-of-care, doxorubicin, in the in vivo SJCRH-30 RMS model. (See TABLE 3.) This combination efficacy study can be done in athymic nude mice as described above. The vehicle used in this study is 20% Captisol® in sterile water and is administered subcutaneously for three consecutive days followed by a four day dosing holiday and repeated for a minimum of four weeks. Doxorubicin (5% dextrose in sterile water) is administered intravenously once weekly while 5-(5-(2-(3-aminopropoxy)-6-methoxyphenyl)-1H-pyrazol-3-ylamino)pyrazine-2-carbonitrile methanesulfonic acid monohydrate (Example 5) is administered in 20% Captisol® in sterile water and subcutaneously for three consecutive days followed by a four day dosing holiday. The treatment period lasts 4 weeks.

Administration of 5-(5-(2-(3-aminopropoxy)-6-methoxyphenyl)-1H-pyrazol-3-ylamino)pyrazine-2-carbonitrile methanesulfonic acid monohydrate (Example 5) as a single agent results in an initial complete response until day 38 at which point tumor regrowth occurs. Treatment of tumors with 5-(5-(2-(3-aminopropoxy)-6-methoxyphenyl)-1H-pyrazol-3-ylamino)pyrazine-2-carbonitrile methanesulfonic acid monohydrate (Example 5) plus doxorubicin results in a complete response and no tumor regrowth. (See TABLE 3; −87% regression, p<0.001.) The combination of 5-(5-(2-(3-aminopropoxy)-6-methoxyphenyl)-1H-pyrazol-3-ylamino)pyrazine-2-carbonitrile methanesulfonic acid monohydrate (Example 5) and doxorubicin appears to be tolerated as there is no significant body weight loss. These results suggest that the combination of 5-(5-(2-(3-aminopropoxy)-6-methoxyphenyl)-1H-pyrazol-3-ylamino)pyrazine-2-carbonitrile methanesulfonic acid monohydrate (Example 5) and doxorubicin may be more effective at inhibiting tumor growth as compared to the sole administration of either agent.

TABLE 3

| Model Name | Histology | Therapeutic Agent(s) | Comparator day | % T/C[1] | % Regression | p-value |
|---|---|---|---|---|---|---|
| SJCRH-30 | RMS | CHK1/2 Inhibitor[2] & Doxorubicin | 56 | NA | −87 | <0.001 |
| SJCRH-30 | RMS | Doxorubicin | 56 | 16 | NA | 0.083 |
| SJCRH-30 | RMS | CHK1/2 Inhibitor[2] | 56 | 58 | NA | 0.105 |
| SJCRH-30 | RMS | CHK1/2 Inhibitor[2] | 46 | 0.1 | NA | <0.001 |
| SJCRH-30 | RMS | ifosphamide | 46 | 34 | NA | 0.001 |
| SJCRH-30 | RMS | irinotecan | 46 | 12 | NA | 0.001 |
| SJCRH-30 | RMS | CHK1/2 Inhibitor[2] + ifosphamide | 46 | NA | −91 | <0.001 |

TABLE 3-continued

| Model Name | Histology | Therapeutic Agent(s) | Comparator day | % T/C[1] | % Regression | p-value |
|---|---|---|---|---|---|---|
| SJCRH-30 | RMS | CHK1/2 Inhibitor[2] + irinotecan | 46 | NA | −86 | <0.001 |

[1]T/C refers to the treated to control value
[2]5-(5-(2-(3-aminopropoxy)-6-methoxyphenyl)-1H-pyrazol-3-ylamino)pyrazine-2-carbonitrile methanesulfonic acid monohydrate (Example 5)

TABLE 4

| Tumor Subtype | Age of Patients at the Time of Tumor Collection (Years) | Result of Treatment with the CHK1/2 Inhibitor[1] |
|---|---|---|
| DSRCT | 20 | 1/1 Complete Response |
| Ewing's Sarcoma | 8-17 | 1/4 Stable Disease |
| Osteosarcoma | 11-19 | 1/4 Stable Disease |
| Alveoloar Rhabdomyosarcoma | 17-24 | 2/2 Complete Response; Acquired Resistance Observed |
| Embryonal Rhabdomyosarcoma | 2-7 | 1/3 Complete Response; 1/3 Stable Disease |
| Leiomyosarcoma | 48-64 | 1/5 Partial Response; 1/5 Stable Disease |
| Liposarcoma | 36-74 | 7/7 Progressive Disease |

[1]5-(5-(2-(3-aminopropoxy)-6-methoxyphenyl)-1H-pyrazol-3-ylamino)pyrazine-2-carbonitrile methanesulfonic acid monohydrate (Example 5)

As illustrated in TABLE 4, pediatric sarcoma cell lines are highly sensitive to in vivo treatment with 5-(5-(2-(3-aminopropoxy)-6-methoxyphenyl)-1H-pyrazol-3-ylamino)pyrazine-2-carbonitrile methanesulfonic acid monohydrate (Example 5). 5-(5-(2-(3-Aminopropoxy)-6-methoxyphenyl)-1H-pyrazol-3-ylamino)pyrazine-2-carbonitrile methanesulfonic acid monohydrate (Example 5) is effective as a single agent in nearly 41% (7/17) of the pediatric sarcoma in vivo mouse models tested, with results ranging from stable disease to complete response. The majority of adult sarcoma models (10/12; 83%) evaluated in vivo were sensitive to single agent treatment with 5-(5-(2-(3-aminopropoxy)-6-methoxyphenyl)-1H-pyrazol-3-ylamino)pyrazine-2-carbonitrile methanesulfonic acid monohydrate (Example 5). Combination of 5-(5-(2-(3-aminopropoxy)-6-methoxyphenyl)-1H-pyrazol-3-ylamino)pyrazine-2-carbonitrile methanesulfonic acid monohydrate (Example 5) with doxorubicin, ifosfamide, or irinotecan appears to circumvent the acquired resistance in SJCRH30 xenografts.

I claim:

1. A method of treating rhabdomyosarcoma consisting of: administering to a patient in need thereof an effective amount of a compound which is 5-(5-(2-(3-aminopropoxy)-6-methoxyphenyl)-1H-pyrazol-3-ylamino)pyrazine-2-carbonitrile, or a pharmaceutically acceptable salt thereof, and administering to the patient irinotecan.

2. The method according to claim 1, wherein the rhabdomyosarcoma is alveolar rhabdomyosarcoma or embryonal rhabdomyosarcoma.

3. The method according to claim 1, wherein the salt is 5-(5-(2-(3-aminopropoxy)-6-methoxyphenyl)-1H-pyrazol-3-ylamino)pyrazine-2-carbonitrile formic acid salt.

4. The method according to claim 1, wherein the salt is 5-(5-(2-(3-aminopropoxy)-6-methoxyphenyl)-1H-pyrazol-3-ylamino)pyrazine-2-carbonitrile dihydrogen chloride salt.

5. The method according to claim 1, wherein the salt is 5-(5-(2-(3-aminopropoxy)-6-methoxyphenyl)-1H-pyrazol-3-ylamino)pyrazine-2-carbonitrile methanesulfonic acid salt.

6. The method according to claim 1, wherein the salt is 5-(5-(2-(3-aminopropoxy)-6-methoxyphenyl)-1H-pyrazol-3-ylamino)pyrazine-2-carbonitrile methanesulfonic acid monohydrate.

7. The method according to claim 1, wherein the salt is 5-(5-(2-(3-aminopropoxy)-6-methoxyphenyl)-1H-pyrazol-3-ylamino)pyrazine-2-carbonitrile methanesulfonic acid monohydrate in crystalline form characterized by a X-ray powder diffraction pattern having peaks at 2θ±0.02°=12.64°, 21.25°, and 26.15°.

8. The method according to claim 1, wherein the compound, or the pharmaceutically acceptable salt thereof, is administered with a pharmaceutically acceptable excipient.

* * * * *